US011391727B2

(12) United States Patent
Beisswenger

(10) Patent No.: US 11,391,727 B2
(45) Date of Patent: Jul. 19, 2022

(54) METHODS FOR IMPROVING CARDIOVASCULAR DISEASE MANAGEMENT

(71) Applicant: PREVENTAGE HEALTHCARE LLC, Lebanon, NH (US)

(72) Inventor: Paul J. Beisswenger, Hanover, NH (US)

(73) Assignee: Journey Biosciences Inc., Lebanon, NH (US)

(*) Notice: Subject to any disclaimer, the term of this patent is extended or adjusted under 35 U.S.C. 154(b) by 239 days.

(21) Appl. No.: 16/621,020

(22) PCT Filed: Jun. 8, 2018

(86) PCT No.: PCT/US2018/036683
§ 371 (c)(1),
(2) Date: Dec. 10, 2019

(87) PCT Pub. No.: WO2018/227106
PCT Pub. Date: Dec. 13, 2018

(65) Prior Publication Data
US 2021/0333268 A1    Oct. 28, 2021

Related U.S. Application Data

(60) Provisional application No. 62/603,787, filed on Jun. 10, 2017.

(51) Int. Cl.
*G01N 33/53* (2006.01)
*G01N 1/40* (2006.01)
(Continued)

(52) U.S. Cl.
CPC ........... *G01N 33/53* (2013.01); *G01N 1/4077* (2013.01); *G01N 30/7233* (2013.01);
(Continued)

(58) Field of Classification Search
CPC .. G01N 33/53; G01N 1/4077; G01N 30/7233; G01N 2001/4088;
(Continued)

(56) References Cited

U.S. PATENT DOCUMENTS 6,323,038 B1    11/2001   Oya et al.
2002/0002203 A1   1/2002   Rahbar
(Continued)

FOREIGN PATENT DOCUMENTS

JP    2000-007700       1/2000
WO   2017/039743 A1    3/2017

OTHER PUBLICATIONS

Holte et al., "Collagen methionine sulfoxide and glucuronidine/LW-1 are markers of coronary artery disease in long-term survivors with type 1 diabetes. The Dialong study," May 13, 2020, PLoS One, p. 1-15, DOI:10.1371/journal.pone.0233174. (Year: 2020).*
(Continued)

*Primary Examiner* — Jennifer Wecker
*Assistant Examiner* — Michael Paul Shimek
(74) *Attorney, Agent, or Firm* — Prince Lobel Tye LLP

(57) ABSTRACT

The present invention provides a method and a kit for determining the risk or rate of an individual of developing diabetes related cardiovascular complications in a subject suffering from either type 1 diabetes mellitus or type 2 diabetes mellitus. The method and the kit comprises: determining the levels of two or more biomarkers purified from a biological sample; wherein said biomarkers are selected from the group comprising lysine advanced glycation end products, arginine advanced glycation end products, and oxidation products; and comparing the determined biomarker levels to standard values, wherein the level of said biomarkers indicate the risk or rate of developing diabetes related cardiovascular disease.

11 Claims, 8 Drawing Sheets

(51) Int. Cl.
    G01N 30/72    (2006.01)
    G01N 30/02    (2006.01)
(52) U.S. Cl.
    CPC ............... G01N 2001/4088 (2013.01); G01N 2030/027 (2013.01); G01N 2560/00 (2013.01); G01N 2800/042 (2013.01); G01N 2800/50 (2013.01)
(58) Field of Classification Search
    CPC ......... G01N 2030/027; G01N 2560/00; G01N 2800/042; G01N 2800/50; G01N 33/50
    See application file for complete search history.

(56) References Cited

U.S. PATENT DOCUMENTS

2013/0143240 A1   6/2013   Marz et al.
2013/0345175 A1*  12/2013  Beisswenger ........... A61P 27/02
                                                        514/86

OTHER PUBLICATIONS

Koska et al., "Advanced Glycation End Products, Oxidation Products, and Incident Cardiovascular Events in Patients With Type 2 Diabetes," Dec. 5, 2017, Diabetes Care vol. 41, American Diabetes Association, p. 570-576, DOI:10.2337/dc17-1740. (Year: 2017).*
Thornally, P. et al., "Quantitative screening of advanced glycation endproducts in cellular and extracellular proteins by tandem mass spectrometry," Biochemical Journal, 2003, vol. 375, pp. 581-592.
Yu, Y. et al., "Advanced glycation end-products and methionine sulphoxide in skin collagen of patients with type 1 diabetes," Diabetologia, 2008, vol. 49, pp. 2488-2496.
Ahmed, N. et al., "Assay of advanced glycation endproducts (AGEs): surveying AGES by chromatograghic assay . . . " Biochem Journal (2002) 364. 1-14.
Ahmed, N. et al., "Degradation products of proteins damaged by glycatlon, oxidation and nitration in clinical type 1 diabetes," Diabetologia (2005) 48: 1590-1603.
Ahmed, N. et al., "Methylglyoxal-Derived Hydroimidazolone Advanced Glycation End-Products of Human Lens Proteins," Ophthalmology & Visual Science, Dec. 2003, vol. 44, No. 12, pp. 5287-5292.
Almuti, K. et al., "Effects of statins beyond lipid lowering: Potential for clinical benefits," International Journal of Cardiology 109 (2006) pp. 7-15.
Baines, J. et al., "Glycoxidation and Lipoxidation in Atherogenesis," Free Radical Biology & Medicine, vol. 28, No. 12, pp. 1708-1716, 2000.
Beisswenger, P. et al., "Early Progeession of Diabetic Nephropathy Correlates With Methylglyoxal-Derived Advanced Glycation End Products," Diabetes Care, vol. 36, Oct. 2013, pp. 3234-3239.
Beisswenger, P. et al., "Increased Collagen-linked Pentosidins Levels and Advanced glycosylation End Products in Early Diabetic Nephropathy," Journal of Clinical Investigation, vol. 92, Jul. 1993, pp. 212-217.
Beisswenger, P. et al., "Metformin inhibition of glycation processes," Diabetes Metabolism, 2003, 29, 6S95-6S103.
Beisswenger, P. et al., "Metformin Reduces Systemic Methylglyoxal Levels in Type 2 Diabetes," Diabetes, vol. 48, Jan. 1999. pp. 198-203.
Beisswenger, P. et al., "Methylglyoxal in diabetes: link to treatment, glycaemic control and biomarkers of complications," Biochemical Society Transactions, vol. 42, Issue 2, Apr. 2014, pp. 450-456.
Beisswenger, P. et al., "Susceptibiltity to Diabetic Nephropathy Is Related to Dicarbonyl and Oxidative Stress," Diabetes, vol. 54, Nov. 2005, pp. 3274-3281.
Brownlee, M., "Glycation Products and the Pathogenesis of Diabetic Complications," Diabetes Care, vol. 15, No. 12, Dec. 1992, pp. 1835-1843.
Choudhuri, S. et al., "Role of N-epsilon-carboxymethyl lysine, advanced glycation end products and reactive oxygen species . . . ,"Molecular Vision 2013, vol. 19, pp. 100-113.
Degenhardt, T. et al., "Chemical Modification of Proteins by Methylglyoxal," Cellular and Molecular Biology, vol. 44, No. 7, pp. 1139-1145.
Dyer, D. et al., "Accumulation of Maillard Reaction Products in Skin Collagen in Diabetes and Aging," Journal of Clinical Investgalion, vol. 91, Jun. 1993, pp. 2463-2469.
Extended European Search Report, dated Jun. 9, 2021, from counterpart EP Application No. 18813021.5.
Fosmark, D. et al., "Increased serum levels of the specific advanced glycation end product methylglyoxal-derived hydroimidazolone . . . " Metabolism Clinical and Experimental, vol. 55, 2006, pp. 232-236.
Geissauf, A. et al., "Formation of N-formylkynurenine suggests the involvement of apoliprotein B-100 centered tryptophan radicals . . . " Federation of European Biochemical Societies Letters, vol. 389, 1996, pp. 136-140.
Genuth, S. et al., "Effect of Intensive Therapy on the Microvascular Complications of Type 1 Diabetes Mellitus," Journal of the American Medical Association, May 15, 2002, vol. 287, No. 19, pp. 2563-2569.
Hammes, H-P. et al., "Aminoguanidine treatment inhibits the development of experimental diabetic retinopathy," Proceedings of the National Academy to Sciences, vol. 88, pp. 11555-11558. Dec. 1991.
Hammes, H-P. et al., "Benfotiamine blocks three major pathways to hyperglycemic damage and prevents experimental diabetic retinopathy," Nature Medicine, vol. 9. No. 3, Mar. 2003, pp. 294-299.
Hirsch, J. et al., "The reaction of some dicarbonyl sugars with aminoguanidine," Carbohydrate Research, vol. 232, 1992, pp. 125-130.
Holman, R. et al., "10-Year Falbw-up of Intensive Glucose Control in Type 2 Diabetes," The New England Journal of Medicine, 2008, vol. 359, No. 15, pp. 1577-1589.
International Search Report for PCT/US2018/036683, dated Jan. 30, 2020.
Kilhovd, B. et al., "Increased Serum Levels of the specific AGE-Compound Methylglyoxal-Derived Hydroimidazolone in Patients with Type 2 Diabetes," Metabolism, vol. 52, No. 2, Feb. 2003, pp. 163-167.
Koschinsky, T. et al., "Orally absorbed reactive glycation products (glycotoxins): An environmental risk factor in diabetic nephropathy," Proceedings of the National Academy of Sciences, vol. 94, pp. 6474, Jun. 1997.
Koska, J. et al., "Advanced Glycation End Products, Oxidation Products, and Incident Cardiovascular Events in Patients With Type 2 Diabetes," Diabetes Care, vol. 41, Mar. 2018, pp. 570-576.
Lieuw-A-Fa, M. et al., "Increased levels of N-epsilon-(carboxymethyl)lysine and N-epsilon-(carboxyethyl)lysine in type 1 diabetic patents . . . " Nephrology Dialysis Transplantation, 2004, vol. 19, No. 3, pp. 631-636.
Liu, B-F. et al., "Methyglyoxal induces apoptosis through activation of p38 mitogen-activated protein kinase to rat mesangial cells," Kidney International, vol. 63, 2003, pp. 947-957.
Lo, T.W.C. et al., "Modification to plasma protein by methylglyoxal under physiological conditions. Prevention by aminoguanidine and L-arginine," Amino Acids, vol. 5, No. 1, 1993, abstract only.
Lu, J. et al., "Increased plasma methylglyoxal level inflammation, and vascular endothelial dysfunction in diabetic nephropathy," Clinical Biochemistry, vol. 44, 2011, pp. 307-311.
Maijer, M. et al., "ACE-I and ARBs in early diabetic nephropathy," Journal of Renin-Angiotensin-Aldosterone System, 2002, vol. 3, No. 4, pp. 262-269.
Mentink, C. et al., "Time course of specific AGEs during optimised glycaemic control in type 2 diabetes," The Netherands Journal of Medicine, Jan. 2006, vol. 64, No. 1, pp. 10-16.
Monnier, V. et al., "Glycation Products as Markers and Predictors of the Progression of Diabetic Complications," Annals of the New York Academy of Sciences, vol. 1043, pp. 567-581, 2005.
Monnier, V. et al., "The Role of the Amadori Product in the Complications of Diabetes," Annals of the New York Academy of Sciences, vol. 1126, pp. 81-86, 2008.

(56) References Cited

OTHER PUBLICATIONS

Nathan, D. et al., "Management of Hyperglycemia in Type 2 Diabetes: A Consensus Algorithm for the Initiation and Adjustment of Therapy," Diabetes Care, vol. 31, No. 1, Jan. 2008, pp. 173-175.
Ogawa, S. et al., "Methylglyoxal Is a Predictor in Type 2 Diabetic Patients of Intima-Media Thickening and elevation of blood Pressure," Hypertension, vol. 56, Sep. 2010, pp. 471-476.
PCT/US2016/00068 International Search Report, dated Oct. 27, 2016.
Perkins, B. et al., "Serum Levels of Advanced Glycation Endproducts and Other Markers of Protein Damage in Early Diabetic Nephropathy in Type 1 Diabetes," PLoS ONE, vol. 7, No. 4, e35655, Apr. 2012.
Pun, P. et al., "Pathological Significance of Mitochondrial Glycation," International Journal of Cell Biology, vol. 2012, Article ID 843505, 2012.
Rabbani, N. et al., "Glycation of LDL by Methylglyoxal Increases Arterial Atherogenicity: A Possible Contributor to Increased Risk of Cardiovascular Disease in Diabetes," Diabetes, vol. 60, Jul. 2011, pp. 1973-1980.
Rodbard, H. et al., "Should the Recommendation of the American Association of Clinical Endocrinologiests for a Hemoglobin A1c Target of 6.5% Be Modified?. . . " Endocrine Practice, vol. 14, No. 6, Sep. 2008, pp. 791-795.
Rosario, R. et al., "Lipids aad Diabetic Nephropathy," Current Diabetes Reports, 2006, No. 6, pp. 455-462.
Saremi, A. et al., "Advanced Glycation End Products, Oxidation Products, and the Extent of Atherosclerosis During the VA Diabetes Trial and Follow-up Study," Diabetes Care, 2017, vol. 40, pp. 591-598.
Saulnier, P-J. et al., "Advanced Glycation End Products Predict Loss of Renal Function and Correlate With Lesions of Diabetic . . . " Diabetes, vol. 65, Dec. 2016, pp. 3744-3753.
Schleicher, E. et al., "Increased Accumulation of the Glycoxidation Product N-epsilon-(carboxymethyl)lysine in Human Tissues in Diabetes and Aging," Journal of Clinical Investigation, vol. 99, No. 3, Feb. 1997, pp. 457-468.
Sell, D. et al., "2-Aminoadipic acid is a marker of protein carbonyl oxidation to the aging human skin: effects of diabetes, renal failure and sepsis," Biochemical Journal, 2007, No. 404, pp. 269-277.
Sell, D. et al., "Pentosidine: a Molecular Marker for the Cumulative Damage to Proteins in Diabetes, Aging and Uremia," Diabetes/Metabolism Reviews, vol. 7, No. 4, pp. 239-251, 1991.
Shcheglova, T. et al., "Reactive Immunization Suppresses Advanced Glycation and Mitigates Diabetic Nephropathy," Journal of the American Society of Nephrology, vol. 20, pp. 1012-1019, 2009.
Stitt, A. et al., "Diabetes-related adduct formation and retinopathy," Journal of Ocular Biology, Diseases and Informatics, 2011, vol. 4, pp. 10-18.

* cited by examiner

FIG. 6A
FIG. 6B
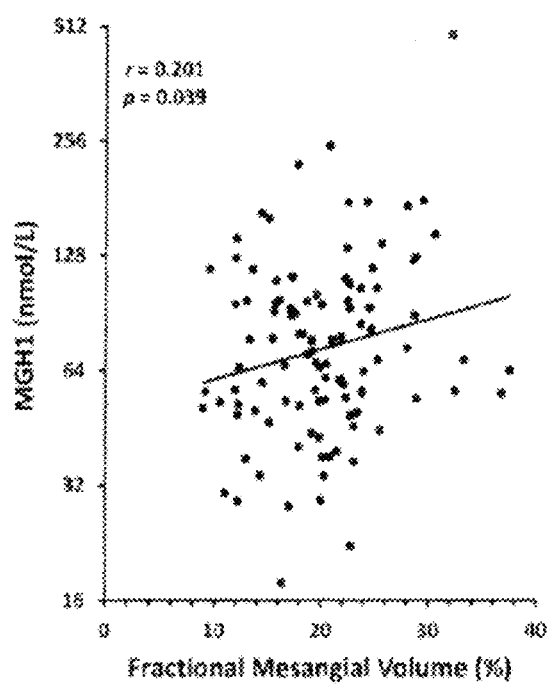
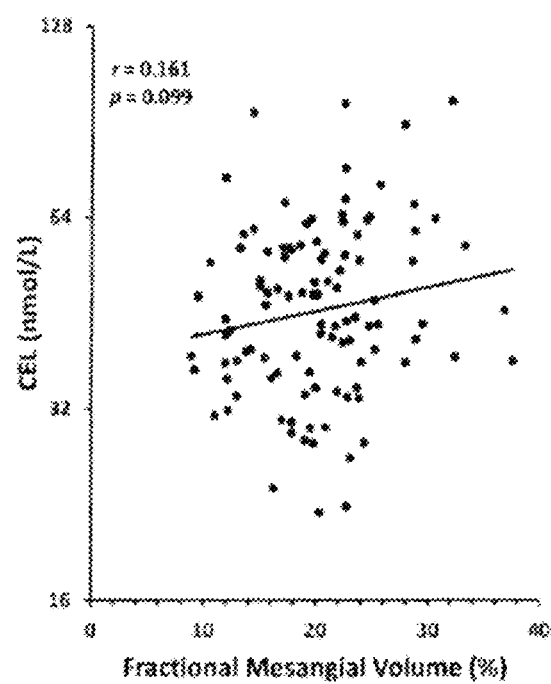

FIG. 7A
FIG. 7B
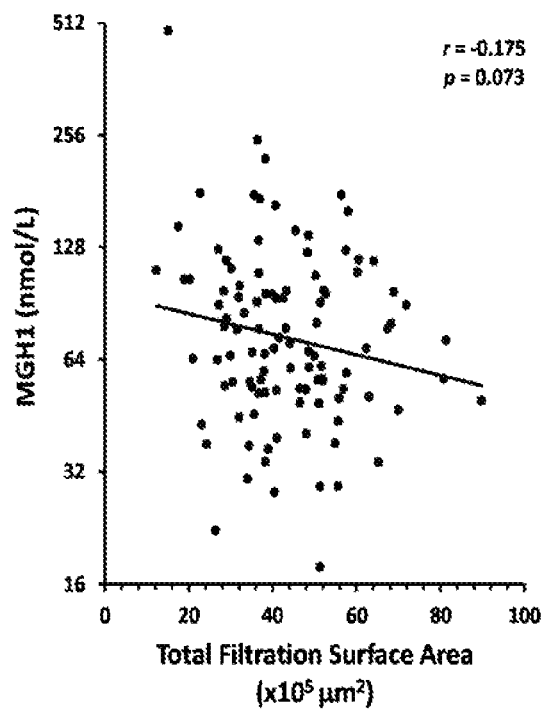
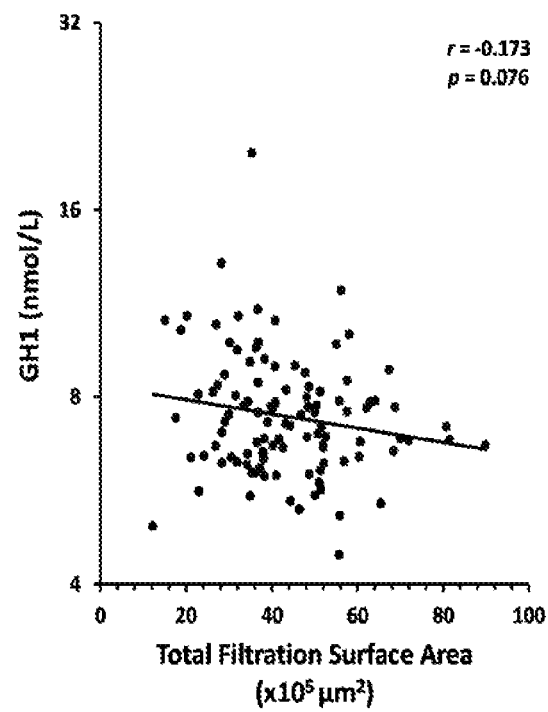

METHODS FOR IMPROVING CARDIOVASCULAR DISEASE MANAGEMENT

CROSS-REFERENCE TO RELATED APPLICATIONS

This application is the National Stage of International Application No. PCT/US2018/036683, filed 8 Jun. 2018, which claims priority to and the benefit of U.S. Provisional Application No. 62/603,787, filed 10 Jun. 2017, entitled "METHODS FOR IMPROVING CARDIOVASCULAR DISEASE MANAGEMENT," which is incorporated herein by reference in its entirety for all purposes.

FIELD OF THE INVENTION

The present invention provides methods for determining the risk of developing, and/or the rate of progression of certain diabetes associated complications (e.g., diabetic nephropathy and other associated disorders) resulting from diabetes related microvascular and/or macrovascular damage in a subject suffering from either type 1 diabetes mellitus or type 2 diabetes mellitus. The present invention also provides methods for handling, storing, and preserving, biological samples (e.g., blood, plasma, and/or urine) from a subject identified as having either type 1 or type 2 diabetes. Further provided are methods for analyzing biological samples from a subject to determine the quantities of one or more biomarkers of interest in comparison to results obtained from previous samples from the subject and/or to results obtained from aggregated samples, or to standards. Further provided are methods for improving the diabetes management in a subject or group of subjects based upon analysis of the risks of developing, and/or the rates of progression of certain diabetes associated complications.

BACKGROUND OF THE INVENTION

Diabetes mellitus (DM) affects more than 30 million people in the United States alone. About 1.9 million people aged 20 years or older were newly diagnosed with diabetes in 2010. Even more staggering to consider, is that an estimated 79 million people aged 20 years or older are believed to have prediabetes, which constitutes 5% of adults aged 20 years or older and 50% of adults aged 65 years or older. (National Diabetes Information Clearinghouse, National Diabetes Statistics, 2011).

Much of the morbidity and cost of diabetes management is attributable to care and control of long-term diabetes-related complications, for example, diabetes is the leading cause of kidney failure, non-traumatic lower limb amputations, and new cases of blindness among adults. Diabetes is also a major cause of heart disease and stroke. After adjusting for population age and sex differences, average medical expenditures among people with diagnosed diabetes were 2.3 times higher than on those without diabetes. The cost of diabetes in 2007 was $175 billion, which includes $116 billion in excess medical expenditures and $58 billion in reduced national productivity. (Dall, et al., Diabetes Care, 31(3):596-615 (2008)).

Based on the current incidence of diabetes and disease demographics, the onset of diabetic complications are on the rise. It has been projected that the number of Americans with diabetic retinopathy will triple to 16 million by 2050. The major cause of the dramatic expansion in rates of end stage renal disease in this country is due to new cases of diabetic nephropathy. Diabetes is now the leading cause of renal insufficiency and end-stage renal disease (ESRD) in the U.S., and the Western world. People with diabetes also have a dramatic increase in the risk of heart attack and stroke. It was primarily treatment of these devastating vascular complications that drove the cost of caring for diabetes to $245 billion in 2012, a 45% increase since 2007.

The chronic elevation of blood glucose level associated with both type 1 and type 2 DM leads to damage of blood vessels producing a disease state called angiopathy. The problems resulting from the angiopathic changes are grouped under "microangiopathy" (due to damage to small blood vessels) and "macroangiopathy" (due to damage to the arteries). The damage to small blood vessels leads to microvascular damage, which can cause diabetic retinopathy and/or diabetic nephropathy. Other prevalent and severe morbid processes associated with the diabetic state are those that mediate an increased risk of cardiovascular disease ("CVD") and cerebrovascular disease, which are seen in subjects with both type 1 and 2 diabetes. The angiopathy associated with diabetes damages both small and larger blood vessels and there are common etiologies associated with the metabolic changes observed in patients with diabetes.

Although diabetic microvascular and macrovascular complications are clearly associated with the degree of hyperglycemia, not all diabetic individuals with poor glycemic control will necessarily develop renal, advanced retinal, or cardiovascular complications. Conversely, some diabetic patients develop severe complications despite having blood glucose concentrations in a range considered satisfactory by many healthcare providers.

The art provides several examples of specific analytes having been the subject of diagnostic methods. For instance, U.S. Pat. No. 6,323,038 discloses a pyridinium compound as a diagnostic reagent for detecting complications associated with diabetes or renal failure. U.S. Publication No. 2011/0079077 discloses urine and serum proteins and their fragments, which alone, or in combination, can be used to diagnose early stage diabetic nephropathy. Nevertheless, the current accepted analytes used in diabetic care, particularly Hemoglobin A1c (HbA1c) which primarily measures hyperglycemia, have significant limitations for pro-actively identifying a subgroup at "high-risk" for developing diabetic angiopathic complications.

The Diabetes Control and Complications Trial ("DCCT") showed that HbA1c (A1C) alone (i.e., that directly indicate the level of glycated hemoglobin in the subject's blood) does not completely determine risk of outcomes. (Beisswenger, et al., Diabetes, 54: 3274-3281 (2005)). The Natural History of Diabetic Nephropathy Study ("NHDNS") showed that only 9% of the risk of progressive glomerular basement membrane ("GBM") thickening in type 1 diabetes is accounted for by the baseline A1C level. The existing analytes and clinical indicators for progression of diabetic retinopathy ("DR") and diabetic nephropathy ("DN"), including retinal morphological changes or the appearance of albuminuria on regular examinations, are unable to identify those at greatest risk during the long 10-20 year "silent phase" when evolving or incipient damage to the kidney, eyes, and cardiovascular ("CV") system are not clinically apparent. (Nathan, et al., N Engl J of Med., 353(25): p. 2643-53 (2005)). By the time these already defined markers become positive, significant damage has frequently already taken place such as substantial pericyte drop-out and avascular capillary (angiogenesis/formation) are present in the retina (Ahmed, et al., Biochem. Soc. Trans., 31(Pt 6):1417-22 (2003)); likewise, substantial irreversible kidney damage can also be present by the time microalbuminuria occurs. (Nathan, et al., N Engl J of Med., 353(25):2643-53 (2005)). It is also widely recognized that CV disease may remain silent for many years, in spite of the gradual accumulation of serious and life-threatening vascular lesions. (Mauer, et al., J. Renin-Angiotensin-Aldosterone System, 3:262-269 (2002); Almuti, et al., Int. J. of Cardiol., 109(1):7-15 (2006)). Unfortunately, exacerbating the situation is the present state of diabetes treatment options such as aggressive treatments for DN such as administration of ACE inhibitors ("ACEIs") and Angiotensin receptor blockers ("ARBs") typically instituted when albuminuria is detected, are unable to slow progression of structural glomerular lesions that lead to DN or progression of DN as was shown by the Renal Angiotensin System Study ("RASS"). (Mauer, et al., J. Renin Angiotensin Aldosterone Syst. 3(4):262-269 (2002); and Mauer, et al., N Engl J Med., 2; 361(1):40-51 (2009)). The inability of existing treatment options such as ACEIs and ARBs to cure/ameliorate diabetic complications suggests that early recognition and upstream prevention of serious diabetic complications such as DN and DR in highly susceptible individuals is far superior approach than waiting for clinical manifestations of diabetic complications prior to beginning diabetic therapies and modifications. The present state of treatment options points to the need for tightly correlated predictions of an individual's risk for progression to serious diabetic complications and thus an upstream initiation of early interventions even during the long silent phase.

Despite there being a longstanding need to accurately predict a subject's risk for diabetes related complications, the failure of the art to devise adequate predictive methods dictates that clinical treatment decisions be made on the faulty premise that all diabetic patients are equally susceptible to complications. However the potential complications associated with type 1 or type 2 diabetes are varied and heretofore unpredictable, and the lack of an adequate predictive test for early prediction of complications leads to large-scale failure in prevention. Reasons for this large-scale failure include the lack of patient specific predictive information, the overwhelming rates of newly discovered diabetes, the massive expense of providing adequate care, the lack of sufficient and adequately trained medical providers, and patient denial of the potential consequences of poor treatment compliance resulting from their lack of accurate individualized predictive information on risk. Diabetes treatments are not only expensive, but some are accompanied by a high-risk of hypoglycemia and drug side effects as well as the expense and risk of new treatments such as pancreatic transplants and the evolving artificial pancreas. Based on these considerations, it will become increasingly difficult to apply many of these therapies to all patients with diabetes, without having better information on individual risk versus benefit projections.

In an attempt to fill the predictive void, several have suggested advanced glycation end products ("AGEs") and oxidation products ("OPs") as possible factors for diabetic complications. Until recently, however, knowledge of these products has been limited to the Early Glycation Products ("EGPs"), several oxidation end products, and a few AGEs. Most prior studies have measured limited numbers of AGEs (See e.g., Yu, et al., Diabetologia, 49(10):2488-98 (2006); Monnier, et al., Annals of the New York Academy of Sciences, (2008); (Beisswenger, et al., Journal of Clinical Investigation, 92(1):212-7 (1993); Dyer, et al., J. Clin. Invest., 91(6): 2463-9 (1993); and Monnier, et al., Annals of the New York Academy of Sciences, 1043:567-581 (2005)), particularly pentosidine and carboxymethyllysine, or have focused on a few end-products that reflect oxidative stress. (See e.g., Yu, et al.; and Baynes, et al., Free Radical Biology & Medicine, 28(12):1708-16 (2000)). A substantial number of these analyses were performed as semi quantitative immunoassays, which have generally not been validated against quantitative chemical analyses. Although some of these studies have shown simple correlations between blood levels of these products and complications (See, Monnier, et al., Annals of the New York Academy of Sciences, 1043: 567-581 (2005)), none have validated their predictive value in large-scale controlled diabetes outcome studies. For instance, a recent study by Perkins, et al., PLoS One, 7(4):335-355 (2012) measuring the levels of AGEs and oxidative markers in LC/MS/MS concluded that there was no correlation between any of the protein damage adduct residues of plasma proteins nor concentrations of related free adducts with subsequent early glomerular filtrate rate (GFR) decline leading to end stage renal disease.

There have been virtually no new biological analytes (e.g., biomarkers) identified for the early detection of diabetic complications over the past 20-30 years. The existing analytes used to try to identify those at a "high-risk" of developing diabetic complications continue to have significant limitations. One of the first signs of diabetic kidney damage is the presence of protein in the urine (micro- or macroalbuminuria). Albuminuria can be assessed using a laboratory test or a simple dip stick test. This test has significant shortcomings since the studies done in those who develop microalbuminuria, actually show that not all of them go on to serious kidney disease. Up to 40% of them show a return to normoalbuminuria. Another 30-40% continue to have microalbuminuria (30-299 mg/gm creatinine on the albumin/creatinine ratio) without showing decline in kidney function and the rest progress to more severe kidney disease. Even when a kidney biopsy is used, which is the gold standard for the diagnosis of DN, there is known to be poor correlation with the level of microalbumin in the urine. (Fioretto, P., et al, Diabetes, 43, 1358-64 (1994)).

Because of the limited predictive value of albuminuria, the serum creatinine levels used to calculate the patient's glomerular filtration rate, is now considered a more accurate test to detect progressive diabetic nephropathy. Furthermore, there are significant limitations of relying on these existing tests since by the time they are detected, considerable kidney damage has already taken place. What is needed are early diagnostic and/or predictive tests in the field of diabetes management, practicable at an early enough stage when effective treatment and management strategies can be implemented to prevent or delay potential diabetes related complications such as diabetic nephropathy and other complications.

SUMMARY OF THE INVENTION

The present invention provides methods for determining the risk of developing, and/or the rate of progression of certain diabetes associated complications (e.g., diabetic nephropathy and other associated disorders including, but not limited to, cardiovascular disease) in subjects suffering from either Type 1 diabetes mellitus or Type 2 diabetes mellitus. These tests will detect underlying diabetes related angiopathic changes in the subject such as microvascular and/or macrovascular damage. The present invention also provides methods for handling, storing, and preserving, biological samples (e.g., blood, plasma, urine) from a subject at risk of complications having either Type 2 or Type 1 diabetes. Further provided are methods for analyzing biological samples from a subject to determine the quantities of one or more biomarkers of interest which will be compared to results obtained from aggregated samples, and/or to standards whether maintained in a database or otherwise. Further provided are methods for improving the diabetes management in a subject or group of subjects based upon analysis of the risks of developing, and/or the rates of progression of certain diabetes associated complications.

Preferred embodiments provide methods for determining the levels of biomarkers, specifically, advanced glycation end products (AGEs) and oxidation products (OPs) in biological samples, including, but not limited to, one or more plasma, plasma ultrafiltrate, or urine samples. These methods are useful in detecting the levels of biomarkers such as $N_\epsilon$-carboxy methyl-lysine (CML); $N_\epsilon$-carboxy ethyl-lysine (CEL); Glyoxal hydroimidazolone (GH1); Methylglyoxal hydroimidazolone (MG-H1); 3-Deoxyglucosone Hydroimidazolone (3DGH); Methionine Sulfoxide (MetSO); and 3-nitrotyrosine (3-NT), Dityrosine, and/or 2-Aminoadipic Acid from one or more biological samples. In preferred embodiments, the biomarker levels in a sample are preferably determined by Liquid Chromatography/Triple Quadrupole Mass Spectroscopy (LC-MS/MS). In one preferred embodiment for measuring biomarkers using LC-MS/MS, the stationary phase is preferably C18 with heptafluorobutyric acid being used as an ion pairing agent. This allows the analysis to be performed with a single column relative as opposed to requiring 2 columns. The present invention further contemplates additional columns types and specificities that will additionally find application with certain other methods of the present invention. For instance, because of its longer chain length, in one such embodiment, perfluroheptanoic acid was tested as an ion-pairing agent in an LC system, using a C18 Synergi RP column. Unexpectedly, however perfluroheptanoic acid did not yield as successful of results as heptafluorobutyric acid in model test systems due to loss of retention of key compounds.

In certain embodiments, counter-ions are included in the sample handling, preparation, and/or testing stages of the present methods. For example, in one embodiment ammonium formate was tested as a counterion based on initial evaluations indicating that this counter-ion might have a beneficial effect on the chromatography when used with PFHA, and thereby shortening the retention times of the late eluting compounds and improving the selectivity of the system. Despite the promising hypothesis for using ammonium formate as a counterion, the particular system was unexpectedly less successful than other methodologies tested.

A method for determining a subject's risk of developing DN or a disorder associated with DN has also been developed. The method includes obtaining a test sample from a subject diagnosed with diabetes (e.g., type 1 or type 2 diabetes), measuring the levels of one or more of $N_\epsilon$-Carboxyethyl Lysine (CEL), Methylglyoxal Hydroimidazolone (MG-H1) and $N_\epsilon$-Carboxymethyl Lysine (CML) and comparing the values to the metabolite levels shown to be associated with either progression or non-progression of diabetic nephropathy. In certain of these embodiments, levels of additional biomarkers of interest (e.g., Methionine Sulfoxide (MetSO), 2-Aminoadipic Acid (AAA), 3-Deoxyglucosone Hydroimidazolone (3-DGH), Glyoxal Hydroimidazolone (G-H1), 3-Nitrotyrosine (3-NT), and/or Dityrosine (DiTyr)) are further measured and compared to metabolite levels shown to be associated with either progression or non-progression of diabetic nephropathy.

Also provided are methods of conducting and/or scheduling diabetic cares and therapies (e.g., drug therapies, behavior modification plans, surgical interventions and organ and cell transplantations, etc.) which include determining a diabetic patient's risk of developing diabetes related kidney disease and/or other diabetes related complications and adjusting the patient's treatment regimen. Treatment regimens include, but are not limited to, glucose lowering agents, additional treatments such as medications that modify the renin-angiotensin system, or specialized diets with low levels of AGEs and/or oxidative products, intended to delay or reduce the severity of diabetes related complications such as kidney, eye or cardiovascular disease. Additional embodiments of the present invention provide methods for developing specific analytically based individualized treatment regimens for one or more patients who are either at risk of developing, or are presently suffering from diabetes related complications.

In still further embodiments, methods are provided for handling and/or analyzing (e.g., correlating) subject derived data related to one or more biomarkers of interest (e.g., CML, CEL and/or MG-H1, MetSO, etc.) in one or more patients who are presently suffering from diabetes or diabetes related complications, or who are at risk of developing diabetes related complications.

In another embodiment, the present invention provides methods of handling subject derived biological samples including, but not limited to, plasma, plasma ultrafiltrates, blood, urine, cells, and/or tissues and the like, such that one or more biomarkers of interest therein are maintained in an suitably assayable state, or a state readily made assayable, for a period of from about 1, 2, 3, . . . 10, 15, 20, 25, . . . 50, 100, 150 hours, months, days, or years, as applicable, to the methods described herein. In certain of these embodiments, the biological samples are maintained in a future assayable state using with one or more ion pairing agents, chelating agents (e.g., heptafluorobutyric acid), counter ions (e.g., ammonium formate), buffers, excipients, stabilizers, cryogenic storage conditions, and/or freeze drying techniques and agents, and the like.

In preferred embodiments, the present invention provides biomarkers that can be used to predict a patient's risk of developing diabetes related complications such as, but not limited to, DN and/or DR, before the patient exhibits known signs and/or markers of organ disease or other diabetes related complications. The present invention further provides methods for predicting a patient's risk of developing, or rate of progression thereof, concerning diabetes related complications during the silent phase of the disease experienced by many patients. More specifically, the present invention provides one or more biomarkers useful for determining a diabetic subject's (e.g., type 1 or type 2) risk of developing kidney disease and/or cardiovascular disease.

The present invention shows that high MetSO levels were associated with lower CVD incidence during the DCCT/EDIC studies. The provided methods significantly improve the predictive value in diabetes healthcare as compared to observation of traditional risk factors. In certain embodiments, baseline level of the AGE CEL predict the risk and/or rate of later progression to cardiovascular disease. Thus, early identification of cardiovascular disease risk in type 1 diabetes is contemplated to facilitate early preventive therapies and better patient outcomes.

In still other embodiments, the present invention provides methods for determining the risk of or rate of developing cardiovascular disease in a subject comprising determining the level of level of one or more biomarkers of interest including, but not limited to, OPs (e.g., MetSO) and/or AGEs (e.g., CEL) present in a biological sample obtained from the subject. In some of these embodiments, the biological samples comprise one or more of blood, plasma, serum, urine, and/or tissue biopsies. In certain preferred embodiments, the sample comprises plasma.

The cardiovascular disease/event related predictive methods of the present invention can be combined with one or more existing heart disease related diagnostic techniques and/or devices, including, but not limited to, electrocardiograms (ECGs) and Holter monitoring devices, echocardiograms, cardiac catheterization, cardiac computerized tomography (CT) scans, and/or cardiac magnetic resonance imaging (MRI).

In still other embodiments, one or more additional methods for determining the level of markers of a cardiovascular disease, as are known in the art, may be used in combination (e.g., prior to, concurrently with, or after the use of) the predictive methods of the present invention to determine the risk of or rate of a subject's developing one or more cardiovascular disease events. The one or more additional marker(s) can be proteins or polypeptides, oligonucleotides, polynucleotides, and nucleic acids, lipids, lipopeptides, lipoproteins, and/or saccharides/carbohydrates (e.g., monosaccharides, disaccharides, oligosaccharides, and polysaccharides), and combinations (e.g., two or more) thereof, that is/are diagnostic of the presence of a cardiovascular disease. For example, diagnostic tests for determining the level of various such markers are commercially available including, but not limited to, test for determining the level of C-reactive protein, B-type natriuretic peptide (e.g., proBNP, NT-proBNP, and BNP), atrial natriuretic peptide (e.g., proANP, NT-proANP, and ANP), cardiac troponin I/T, C-reactive protein, creatinine, blood urea nitrogen (BUN), liver function enzymes, albumin, and/or bacterial endotoxin. Additional non-limiting markers of a cardiovascular disease are described in U.S. Patent Application Publication Nos.: 2007/0248981; 2011/0053170; 2010/0009356; 2010/0055683; and 2009/0264779 (each of which is hereby incorporated by reference).

Additional embodiments, further provide for preparation of a report describing the patient's risk of developing, or rate of progression, of one or more diabetes related complications. Reports may additionally, or solely, be directed to describing the patient's risk of developing, or rate of progression, to cardiovascular disease. Suitable reports can be produced either manually by a technician and/or at least in part complied electronically from one or more databases and electronic sources. The reports can be sent and/or transmitted (e.g., electronically or otherwise) to one or more recipients or groups of recipients including, but not limited to, a patient, a guardian or other designee of a patient, a physician or other clinician, and/or a medical (e.g., diabetes or cardiovascular disease) counselor or care provide, a hospital and/or care facility, a residential or rehabilitation care facility, an insurance provider, and the like. The present invention further contemplates maintaining a repository of individual reports wherein future access may be controlled and incident to fees (e.g., subscription, license, and/or sale) received for access to the data, reports, or transmissions.

Still further embodiments provide kits comprising the one or more, preferably all, of the materials necessary for practicing the described methods of the present invention following obtention of suitable patient samples (e.g., blood, plasma, urine, and the like). Kits preferable further comprise instructions and/or documentation for practicing the methods of the present invention.

The present invention also provides, in other embodiments, methods of identifying a subject at risk of developing diabetes related complications such as, but not limited to, kidney disease, eye disease, or cardiovascular disease.

BRIEF DESCRIPTION OF THE DRAWINGS

FIGS. 6A and 6B show partial residual plots of fractional mesangial volume analyses as adjusted for: age, sex, treatment assignment, diabetes duration, HbA1c, MAP, GFR, and ACR.

FIGS. 7A and 7B show partial residual plots of total filtration surface area analyses adjusted for: age, sex, treatment assignment, diabetes duration, HbA1c, MAP, GFR, and ACR.

DETAILED DESCRIPTION OF THE INVENTION

I. Definitions

Figure 1:
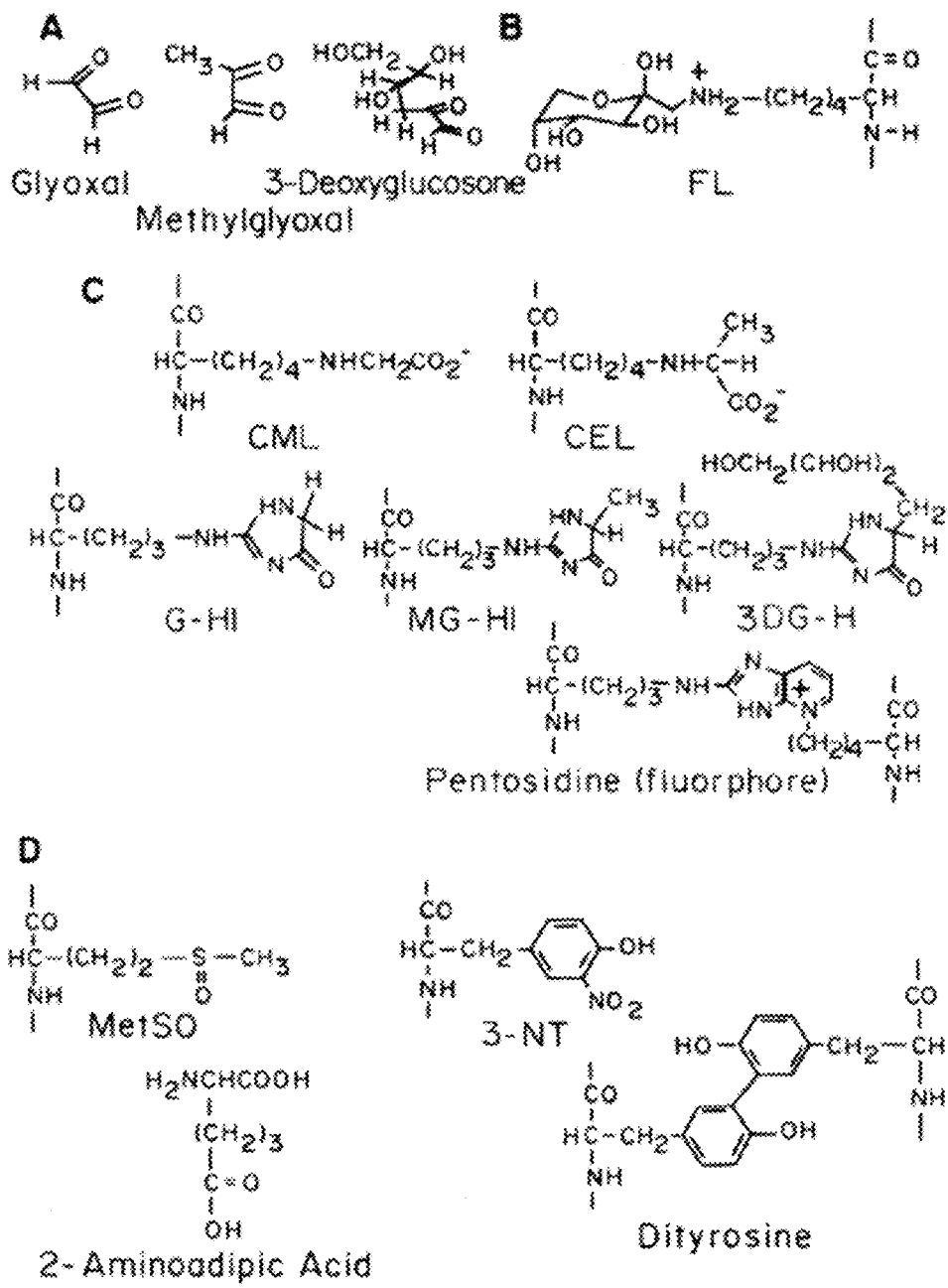
FIG. 1 shows the chemical structures of biomarkers FL=$N_\varepsilon$-Fructosyllysine; CML=$N_\varepsilon$-Carboxymethyl Lysine; CEL=$N_\varepsilon$-Carboxyethyl Lysine; G-H1=Glyoxal Hydroimidazolone; MG-H1=Methylglyoxal hydroimidazolone; 3DG-H=3-Deoxyglucosone Hydroimidazolone; MetSO=Methionine Sulfoxide; 3-NT=3-Ditrotyrosine.

As used herein, the term "A disorder (or condition) associated with diabetic nephropathy" refers to a disorder that stems from angiopathy of capillaries in the kidney glomeruli. Non-limiting examples of associated disorders may include nephrotic syndrome, chronic kidney failure, and end-stage kidney disease. "Diabetic nephropathy" as used herein refers to a disorder characterized by angiopathy of capillaries in the kidney glomeruli. The term encompasses Kimmelstiel-Wilson syndrome, nodular diabetic glomerulosclerosis and intercapillary glomerulonephritis.

As used herein, the term "cardiovascular disease" refers to a disorder of the heart and blood vessels, and includes disorders of the arteries, veins, arterioles, venules, and capillaries. Non-limiting examples of cardiovascular diseases include cardiac hypertrophy, myocardial infarction, stroke, arteriosclerosis, confirmed angina, congestive heart failure, and coronary revascularization. Additional examples of cardiovascular diseases are known in the art.

As used herein, the terms "elevated" or "elevation" are meant a difference, e.g., the presence of a statistically significant or detectable increase in a determined or measured level of a biomarker of interest (e.g., OPs and/or a AGEs) as compared to a reference level of the same biomarker in a subject not having one or more symptoms or indicia of disease, having a propensity to develop a disease, or recognized medical conditions. In some embodiments, the reference is a threshold level, and any level above that is considered "elevated." Likewise, the measured level of biomarker of interest that is below, or less than, the level of the same biomarker is "depressed," "decreased," or "lessened" and equivalents.

As used herein, the terms "reference level" or "standard value" are meant to mean a threshold level or a level in a control subject or control patient population. A reference level will depend on the assay performed and can be determined by one of ordinary skill in the art using suitable methods and assays known in the art or using the methods of the present invention on a significant population of interest.

As used herein, the terms the term "hypertriglyceridemia" is meant a triglyceride level that is greater than or equal to 180 ng/mL (e.g., ≥200 ng/mL).

As used herein, the term "hypercholesterolemia" is meant an increased level of at least one form of cholesterol or total cholesterol in a subject. For example, a subject with hypercholesterolemia can have a high density lipoprotein (HDL) level of ≥40 mg/dL (e.g., ≥50 mg/dL or ≥60 mg/mL), a low density lipoprotein (LDL) level of ≥130 mg/dL (e.g., ≥160 mg/dL or ≥200 mg/dL), and/or a total cholesterol level of ≥200 mg/dL (e.g., ≥240 mg/dL).

As used herein, the term "hypertension" is meant an increased level of systolic and/or diastolic blood pressure. For example, a subject with hypertension can have a systolic blood pressure that is ≥120 mmHg (e.g., ≥140 mmHg or ≥160 mmHg) and/or a diastolic blood pressure that is ≥80 mmHg (e.g., ≥90 mmHg or ≥100 mmHg).

The terms "patient(s)" and "subject(s)," as used herein, are understood to include single individuals and groups of individuals (i.e., two or more) as the particular case indicates. Suitable patients and/or subjects include mammals. Suitable mammalian patients and/or subjects are understood to include, but are not limited to, humans. Accordingly, suitable mammalian patients and/or subjects further include companion animals (e.g., canines felines, and/or equines, etc.) as well as production animals (e.g., bovines, and/or porcine, etc.).

As used herein, the term "database" comprises any combination of one or more structured or unstructured information repositories. In certain preferred embodiments, a database in whole or in part comprises standard values for one or more biomarkers of interest in a sample or a population of samples (e.g., biological samples from one or more human subjects diagnosed with, or not diagnosed with, diabetes). No distinction is intended between whether a database is disposed "on" or "in" a computer readable medium. In preferred embodiments, a database is accessible from or stored permanently or semi-permanently in a computer readable medium.

II. Method for Predicting a Patient's Risk of Developing Diabetic Nephropathy

A. Markers to be Assessed

Specific chemical end products have been identified in carefully documented outcome studies based on investigation of the activation of specific glycation and oxidative pathways in clinical populations with documented nephropathy and retinopathy. These pathways lead to the formation of a spectrum of early glycation products (EGPs), including the chemically reactive α dicarbonyl compounds, methylglyoxal (MG), 3-deoxyglucosone (3DG), and glyoxal (G). The α-dicarbonyls, in turn, lead to the formation of later stage chemical reactions to form advanced glycation end products (AGEs), in processes that are independent from HbA1c formation. Increased glucose-induced oxidative stress (OS) may also be caused by inherent differences in processes that control cellular oxidative mechanisms, which can directly and independently activate major pathways that produce diabetic complications. It has been found that both dicarbonyl stress and OS are selectively activated in those prone to diabetic complications (i.e., high risk subpopulations), resulting in higher levels of glycated and oxidized protein and lipid byproducts, but not directly to changes in HbA1c.

The present invention provides assays to assess blood and urine levels of selected glycation and oxidative end products of these chemical pathways have been developed to make the measurements more precise. While not limited to any particular mechanism of action, it is contemplated that since these end products (i.e., AGEs and OPs) represent slowly turning over end products of glycative and oxidative pathways, their use in clinical outcome studies is superior to measurement of short acting chemical precursors that do not necessarily reflect long-term overproduction when checked in one or more biological samples such as blood, plasma, and/or urine samples.

In these studies it was found that the quantitatively highest in vivo AGEs in type 1 diabetes are hydroimidazolones (HI) derived from arginine residues modified by methylglyoxal (MG), 3-deoxyglucosone (3DG), and glyoxal, produced in turn from their individual synthetic pathways. Other quantifiable AGEs in these studies include glyoxal-lysine derived carboxymethyl (CML), and the MG-lysine product, carboxyethyl-lysine (CEL). Markers of oxidation and nitration, including methionine sulfoxide (MetSO), formed by the oxidation of methionine, 2-Aminoadipic Acid formed from lysine residues, as well as other markers of nitrosive damage leading to production of 3-Nitrotyrosine (3-NT) and Dityrosine have also been measured. It has been found that substantial differences exist between diabetic and control populations (about 5 to 15 fold). The unprecedented increases observed in AGEs and OPs in diabetes, and the substantial differences observed between individuals, indicate that these biomarker levels, alone or in addition to HbA1c, have the potential to markedly sharpen the ability to differentiate subjects at very high versus very low risk of developing diabetes related complications. The key AGEs and OPs of interest that are most predictive of complications, including hydroimidazolones and MetSO, showed no correlation with HbA1c, suggesting that they are produced by chemical pathways that relate to complications, but respond uniquely to the level of glycemia based on individual patient characteristics.

In preferred embodiments, AGEs and OPs biomarkers are measured in plasma and/or urine samples to assess a patient's risk of developing diabetic nephropathy or other complications. By comparing the levels in carefully defined nephropathy progressors and non-progressors, the levels of specific AGE's allow determination of a diabetic subject's risk of developing diabetes related DN or a disorder associated with DN. In a more preferred embodiment, plasma filtrate levels of three AGEs (i.e., $N_\varepsilon$-CarboxymethylLysine (CML); $N_\varepsilon$-Carboxyethyl Lysine (CEL), and/or Methylglyoxal Hydroimidazolone (MG-H1)), alone or in combination with HbA1c, are indicators of early progression of DN. In an even more preferred embodiment, MG-H1 levels alone are an independent predictor of a subject's risk of developing DN. The methods described herein can be used to quantify the following products, which are shown in FIG. 1.

Arginine derived AGEs: These biomarkers include hydroimidazolones (HI); which are AGEs derived from arginine residues modified by glyoxal, MG, and 3-DG and include GH1 (glyoxal hydroimidazolone), MG-H1 (Methylglyoxal Hydroimidazolone), and 3DG-H (3-Deoxyglucosone Hydroimidazolone), respectively.

Lysine derived AGEs: Other AGEs that can be measured are lysine-based and include glyoxal derived Nε-carboxymethyl-lysine (CML), and MG derived Nε-Carboxyethyl Lysine (CEL). (Thornalley, et al., Biochemical Journal, 375(Pt 3):581-92 (2003)). Other AGEs that can be measured include the more traditional product, pentosidine, which is measured by HPLC and fluorescence detection (See, Sell, et al., Diabetes, 40(Suppl I):302A (1991)).

Quantitative markers of oxidative damage to proteins can also be measured and include methionine sulfoxide (MetSO), formed by the oxidation of the sulfhydryl group on Methionine. (Yu, et al., Diabetologia, 49(10):2488-98 (2006)). The tyrosine cross-link, Dityrosine, as well as a widely studied marker of combined oxidative/nitration damage to proteins, 3-Nitrotyrosine (3-NT) can also be measured in other embodiments. (Geibauf, FEBS Letters, 389:136-140 (1996)). To amplify the information obtained on the role of oxidative stress in the development of diabetic complications, another unique oxidative product, 2-Aminoadipic Acid, a product resulting from metal catalyzed oxidation of lysyl residues (Sell, Biochemical J., 404(2):269-77 (2007)) is further measured in still additional embodiments.

Urine creatinine levels can also be determined to provide uniform expression of product/creatinine urine analyte content. The urinary and serum "free fraction" determinations allow the calculation of renal clearance rates of each analyte.

Data obtained in landmark outcome studies with type 1 diabetes, are applicable to patients with type 2 diabetes. It is well recognized that major clinical trials have shown a similar significant relationships between glycemic control and progression of DN and DR in both type 1 and type 2 diabetes as was shown in the DCCT and The United Kingdom Prospective Diabetes Study ("UKPDS") (DCCT/EDIC, JAMA, 287(19):2563-9 (2002); Holman, et al., N Engl J Med., 359(15):1577-89 (2008)), suggesting similarities in pathogenesis for both diabetes types. These considerations have led the American Diabetes Association (ADA), American Association of Clinical Endocrinologists (AACE), and European association for the Study of Diabetes (EASD) to recommend similar HbA1c guidelines to prevent DR and DN in both type 1 and 2 diabetes. (See e.g., Nathan, et al., Diabetes Care, 31(1):173-5 (2008); and Rodbard, et al., Endocrine Practice, 14(6):791-5. (2008)).

B. Sample Collection

Preferably the methods of collection, storage, and processing of samples are tightly controlled as described herein because improper handling can lead to artifactual sample oxidation. It has been found that many AGEs measured in stored plasma samples are stable over multiple years. Acceptable stability has been confirmed by observing similar levels of analytes, when compared to levels in plasma samples stored at −80° C. for 10-15 years with those in freshly drawn plasma from diabetic subjects.

Preferably, during sample preparation, steps are taken to prevent formation of artifacts. For example, one or more of the following steps are contemplated for sample collection, storage, and or preparation prior to testing: rapid separation of red blood cells from plasma at 4° C.; use of chelating agents such as EDTA in blood samples; addition of a preservatives or antioxidants such as butylated hydroxytoluene (BHT); immediate snap freezing such as on dry ice; and/or storage at −80° C. are exemplary of steps that can be taken to minimize formation of artefacts.

In one preferred embodiment, plasma samples are collected by a carefully defined protocol, including collection in EDTA, immediate spinning to sediment red blood cells (RBCs), separating plasma from RBCs at 4° C., followed by immediate freezing and long-term storage at −80° C. In one embodiment, using this process MetSO levels were in the expected range when compared with the same samples not handled accordingly that showed artifactual OS in serum.

Based on these observations, in preferred embodiments, plasma biological samples are preferred for measurement of OP and AGEs in stored samples since it contains the chelating agent (EDTA) and is immediately spun and separated from RBCs after collection, and flash frozen. Serum, on the other hand, has to undergo clotting at room temperature before separation and storage, thus exposing proteins to leukocyte myeloperoxidase and other pro-oxidant enzymes. Serum also contains no chelator of trace metals (Fe and Cu), both of which can promote spontaneous in vitro oxidative stress.

In a preferred method, a plasma sample is collected from a subject diagnosed with either type 1 or type 2 diabetes and the levels of one or more of the biomarkers are subsequently determined. The preferred sample is a plasma ultrafiltrate. This free fraction can be prepared by centrifugation at 4° C. through microspin filters (10,000 MW filter cut-off, 50 µl aliquot). The rational for measuring this fraction is that cells maintain the quality and functional integrity of proteins by degradation and replacement of proteins damaged by oxidation and glycation. (See, Thornalley, et al., Biochemical Journal, 375(Pt 3):581-92 (2003), and Goldberg, et al., Nature, 426(6968):895-9 (2003)). This occurs by proteolysis, liberating the oxidized, glycated, and nitrated, amino acids as free adducts, which in turn are released into blood plasma and excreted in urine. (See, Thornalley, et al., Biochemical Journal, 375(Pt 3):581-92 (2003)). Since these free adducts are released into blood plasma as tissue breakdown of AGEs occurs, changes in plasma concentrations reflects tissue damage in diabetes, while providing new markers indicative of the damaging effects of hyperglycemia.

Adduct residues chemically react with and become bound to plasma proteins. Accordingly, in some embodiments, since some of the products are acid labile, chemically bound products are determined after exhaustive sequential enzymatic digests using suitable enzymes. Examples of enzymes that can be used include but, are not limited to, pepsin, Pronase E, Aminopeptidase and prolidase. Methods for digesting product chemically bound to plasma proteins are described in Ahmed, et al., Biochemical Journal, 364(Pt 1):1-14 (2002).

In certain embodiments, where the biological samples tested comprise urine, the biomarkers in the urine are preferably measured from a urine filtrate that is prepared by centrifugation at 4° C. through microspin filters (10,000 MW filter cut-off). Methods for preparing a urine filtrates are described, for example, in Ahmed, et al., Diabetologia, 48:1590-1603 (2005).

It has been found that systems such as an Agilent Model 6490 Triple Quadrupole MS System with a 1290 Infinity LC System for Ultra high pressure liquid chromatography (UHPLC) (Wilmington, Del.) provide about a 1000 fold increase in analytical sensitivity over other instruments, and a four-fold improvement in sample throughput. HPLC methodologies using ion pairing agents and techniques can be used to resolve the complex mixture of compounds, but they can have several drawbacks that need to be considered. Such as, ion-pairing agents tend to cause difficulties with HPLC pump performance, thus vigilance and frequent pump washings are needed to keep the systems working properly, ion-pairing systems require long re-equilibration times making it more difficult to design a high throughput environment, and finally, ion-pairing agents can cause ion-suppression and potential loss of signal of target compounds. The present invention provides optimized methods for successfully using ion-paring agents in certain embodiments. Those skilled it having the benefit of the teachings of the present invention will be able to select ion-paring agents and testing conditions for optimal predictive results.

In still other embodiments, another useful methodology is hydrophilic interaction chromatography (HILIC). Like normal phase chromatography, the order of elution for compounds is reversed with the more hydrophobic compounds eluting early and the more hydrophilic compounds being retained in the column, providing several advantages including enhanced retention of the hydrophilic compounds that are present in the mix of compounds and unique selectivity that may help resolve some of the previously co-eluting peaks. Buffers used in this system are ideal for MS/MS detection (low backgrounds and ion suppression). Changing pH of the system can give an alternate method for modifying the selectivity of the system. In certain embodiments, columns comprising advanced core-shell technology or UHPLC configurations, that are amenable to high throughput applications, including the Agilent Porous Shell Technology (Agilent Technologies Inc., Santa Clara, Calif.), are favorably employed in various embodiments of the present invention.

Additional embodiments of the present invention provide methods that utilize C18 stationary phases, preferably which have been suitably modified for different selectivities and enhanced retention of polar compounds. Modification of buffer pH with some of these alternate systems should lead to better retention and different compound selectivities. Some examples of this technology include Synergi Polar-RP (Phenomenex Inc., Torrance, Calif.) with an ether linked phenyl group for retention of polar compounds without ion-pairing, or Luna $NH_2$ phase (Phenomenex Inc.) for polar selectivity and a weak anion exchange capability, that can be utilized at a higher buffer pH to increase retention of polar compounds in certain embodiments.

Mixed-mode stationary phases in HPLC methodologies are further contemplated for use in additional embodiments. Exemplary columns combine C18 and ion exchange capabilities into one unit (column). Many times the ion-exchange capability can mimic the effects of an ion-pairing agent. Accordingly, mixed mode column(s) with cation exchange capabilities are specifically contemplated in some embodiments.

C. Biomarker Assay and Determination of Risk for Developing DN

In one preferred embodiment, the level of biomarkers in the plasma and urine prepared as discussed above are determined by Liquid Chromatography/Triple Quadrupole Mass Spectroscopy (LC-MS/MS). Utilizing methods involving carefully modified conditions, wherein the biomarkers of interest are measured utilizing internal standardization by stable isotope substituted standards.

To determine the optimal sample number required to provide a representative estimate of each of the plasma and urinary biomarkers over time, multiple measurements were used to calculate an acceptable quantitative estimate of each analyte. A representative calculation by this approach follows based on measurement of the urinary AGE, pentosidine, in 4-6 samples/diabetic subjects for ten subjects, over 5 years. For these measurements, it was determined that between person variance=$7.64 \times 10^{-7}$ and within person variance=$2.06 \times 10^{-6}$. Thus Total Variance=Between person variance+Within person variance=$7.64 \times 10^{-7} + 2.06 \times 10^{-6} = 2.82 \times 10^{-6}$. For the mean of N observations from the same person, the Variance of Mean would then=Between person variance+Within person variance/N or $7.64 \times 10^{-7} + 2.06 \times 10^{-6}/N$.

Based on these calculations, one can then determine if the within person variance of the mean is less than the between person component. As shown in the Table 1 below N=3 will achieve this aim since $2.06 \times 10^{-6}/3 = 6.87 \times 10^{-7}$ which is less than the $1.45 \times 10^{-6}$ variance of mean value ($3^{rd}$ line in table). For sample sizes more than four, little is gained in these studies by increasing the number of analyses since each additional observation gives <5% total reduction from a sample size of 1.

A database has been compiled of the levels of the various biomarkers that are indicative of the patients at risk of developing kidney disease or other complications. Non-diabetic levels are about ⅓ to ¼ of those seen in diabetics, as shown in Table 1. In one embodiment, levels of CEL<0.042 (0.020-0.042), MG-H1<0.103 (0.030-0.103) and CML<0.062 (0.033-0.062) indicate a 94% chance that the individual is protected from DN (in the lower tertile of change).

The levels of the three products were significantly higher in the fast progressors (upper quartile of GBM change) relative to the non-progressors. This analysis was performed by a Wilcoxon method.

TABLE 1

AGEs as Early Indicators of DN

| Biomarker (All nM) | FP Mean ± SD | SP Mean ± SD | P- Value (Wilcoxon) |
| --- | --- | --- | --- |
| CML | 0.088 ± 0.022 | 0.075 ± 0.023 | 0.003 |
| MG-H1 | 0.200 ± 0.099 | 0.165 ± 0.127 | 0.040 |
| CEL | 0.058 ± 0.015 | 0.049 ± 0.015 | 0.026 |

Linear regression analysis of any product or products versus progressive thickening of the GBM (DN progression) shows that the square of the R (correlation coefficient), which is a measure of the degree of prediction for each biomarker, was greater for the three biomarkers with HbA1c relative to HbA1c alone. For example, in Table 2, HbA1c accounts for 4.7% of predictive value (0.047), CML 0.026%, etc. The sum of the three biomarkers plus A1c was 11.6%. The value of measuring a biomarker one time is additive to A1c.

TABLE 2

Linear Regression of AGEs as Early Indicators of DN

| Variables in Regression Model | % of explained variation (r-squared) | |
|---|---|---|
| | GBM | MES |
| CEL | 0.026 | 0.002 |
| CML | 0.026 | 0.01 |
| MGH1 | 0.006 | 0.005 |
| HbA1c | 0.047 | 0.027 |
| A1c + CEL | 0.073 | 0.029 |
| A1c + CML | 0.065 | 0.034 |
| A1c + MG-H1 | 0.051 | 0.031 |
| A1c + CEL, CML, MG-H1 | 0.116 | 0.052 |

Another type of analysis is the Logistical Regression analysis which allows one to calculate an odds ratio. This allows one to predict the increase in risk of progression to dN in a linear fashion relative to the level of each product. In one embodiment, this is contemplated as probably the closest to quantitative prediction of risk and as described herein, predicts a about a 10 to 50% risk.

The lower tertile of values for the three biomarkers showed that for CEL<0.042 (0.020-0.042), MG-H1<0.103 (0.030-0.103) and CML<0.062 (0.033-0.062), there was a 94% chance that the individual is protected from DN (in the lower tertile of change).

Each of the three biomarkers are individually predictive of progression to DN in combination with HbA1c, and the sum of the increased predictive power of kidney change (increased GMB width) is increased from 4.7% for one measurement of A1c, to 11.6% for the three biomarkers. This represents an increase of 7.9% which is 2.5 fold or 247% greater than HbA1c alone.

Figure 2A:
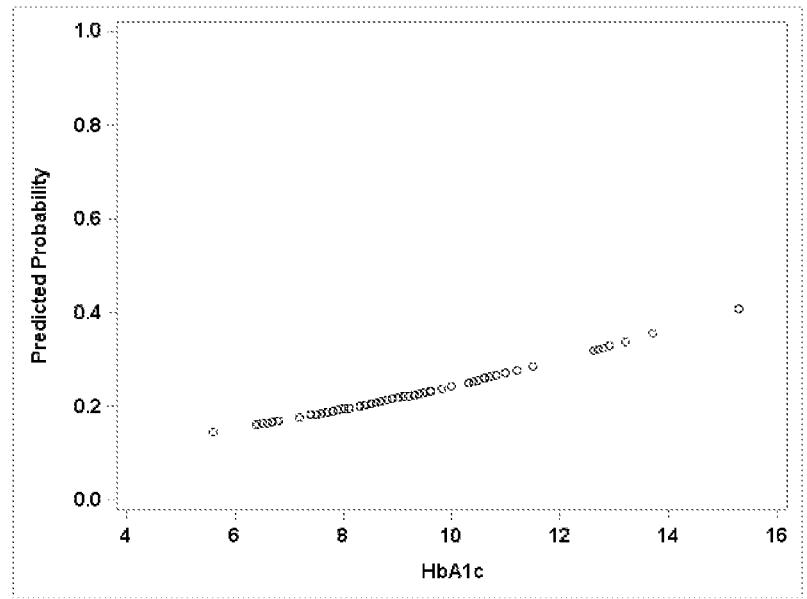
FIGS. 2A-2D show a logistic regression models used to develop predictive equations relating each biomarker to the probability of a subject's classification as a "fast" progression (FP) of DN. CML and MG-H1 values were log transformed when used as predictors and then back-transformed when creating predictive probability plots. For the 3 biomarkers, but not for HbA1C (p=0.28) measured at the same time, there was a significant relationship to the probability of classification as a FP (CML p=0.02; CEL p=0.03; MG-H1 p=0.048). For HbA1c, the relationship was significant when fit to the entire sample (n=186) over 5 years (p=0.006).
Figure 2B:
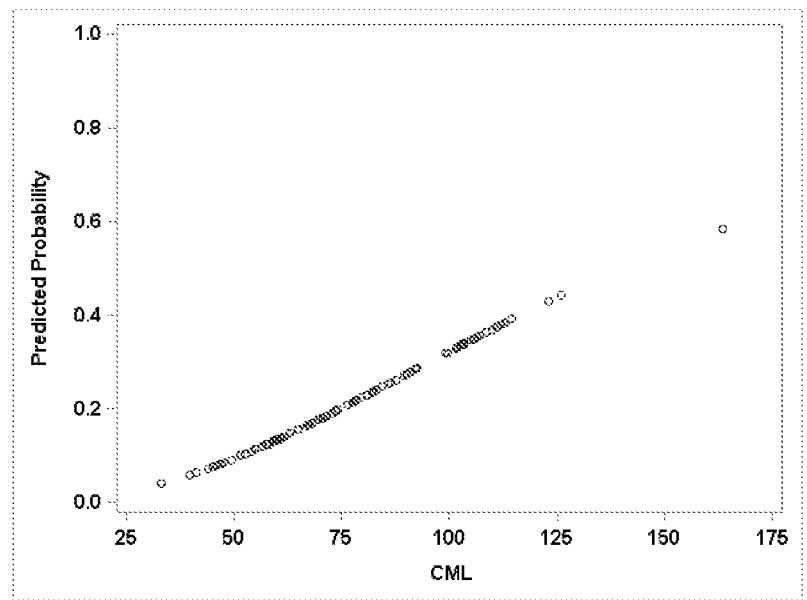
Figure 2C:
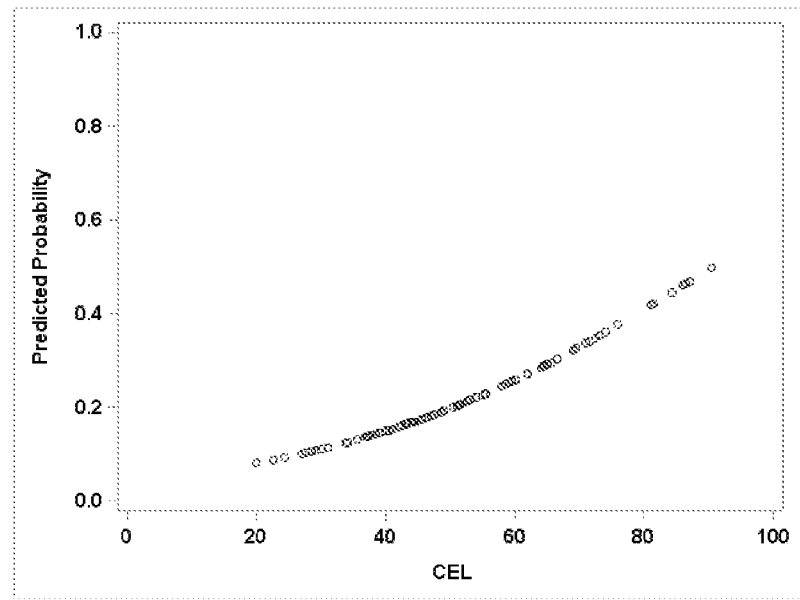
Figure 2D:
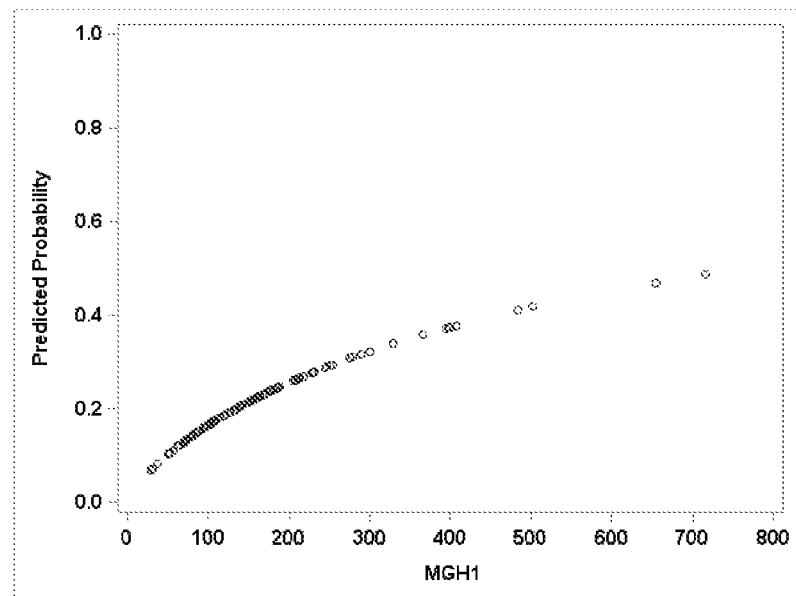

Analyses performed by logistical regression show the odds of progression of DN (y axis) relative to the levels of the 3 biomarkers (X axis) (FIGS. 2B-2D), relative HbA1c (FIG. 2A). The Odds ratio for progression for CEL, MG-H1 and CML biomarkers is 68 to 92% for each one standard deviation of change is provided in Table 3, below.

TABLE 3

Odds Ratios for Prediction of Rapid Progression of DN by A1c or AGEs

| Biomarker | Odds Ratio | 95% Confidence Interval | Value of 1 SD Change |
|---|---|---|---|
| HbA1C | 1.29 | (0.82, 2.02) | 1.74 |
| CML (log) | 1.95 | (1.14, 3.35) | 0.0157 |
| CEL | 1.72 | (1.06, 2.77) | 0.303 |
| MGH1 (log) | 1.68 | (1.004, 2.81) | 0.561 |

Ten native and internal stable heavy isotope substituted AGE and OP standards were procured from commercially available sources, or by custom synthesis, to create a database. Commercially available standards include CML, CEL, G-H1, MG-H1, and 3DG-H. Oxidative end products (OPs) included MetSO, 3-NT, AAA, and DiTyr.

These precision diagnostic tests assess an individual diabetic patient's risk of developing specific complications associated with their disease. These precision diagnostic tests are preferably performed on biological samples (e.g., blood samples) submitted to a central clinical laboratory facility. In a preferred embodiment, the tests identify the presence and amount of from one to ten AGEs and OPs biomarkers (biomolecules). A risk profile for the development of diabetic complications, based on a comparison with data obtained from individuals without disease as well as at various confirmed stages of disease, is constructed. This information is sent to the ordering physician to deliver improved care by specifically adjusting treatments to an individual patient's profile or to others in the patient care system and support network. Alternatively, a simplified, or detailed, report can be sent directly to the patient. With increasing focus on individualized, cost-effective treatment plans for patients, access to this information will become increasingly valuable and necessary in the marketplace.

III. Methods of Diabetic Care

The methods described herein allow healthcare providers to select risk and cost appropriate therapeutic regimens for diabetic individuals to achieve appropriate levels of glycemic control to delay or prevent diabetes associated complications such as DN, DR, and/or cardiovascular disease. It is contemplated that the present biomarkers and associated methods have more than three times the predictive value for renal complications as compared to the current "gold standard," being Hemoglobin A1C (HbA1C). Additionally, it is further contemplated that the biomarkers of interest can be early predictors of propensity to progress to (or risk of developing) retinopathy, vascular disease, and risk of heart attack and stroke. Diagnostic tests that predict early progression of these complications before symptoms are visible allow doctors and patients to make individual adjustments in treatments and behavior that could significantly improve outcomes. Enhanced outcomes will improve lives and save billions of health care dollars annually.

The current paradigm for diabetes care is one of "one size fits all." Parameters are set for all patients, and aggressive specialized treatments are offered either to those who can pay for them or for those who are already experiencing significant complications. The treatment of diabetes is often done with tests that provide retrospective information about what has already happened, followed by "catch-up" treatments to deal with problems, rather than proactive individualized treatments to prevent those that are to come. Although aggressive diabetes treatments that are required for highly susceptible individuals can be cost effective in the long run, they are sometimes more expensive in the short run, and are likely to be accompanied by a higher risk of hypoglycemia and drug side effects. Therefore early identification of high-risk individuals is necessary to balance the potential benefit against the increased risk and expense of new pharmacologic agents and newly evolving high-tech treatments. The glycation/oxidation based diagnostic assays should significantly change preventative interventions by allowing the identification those at high, medium, moderate, or low risk of diabetic complications during the earliest stages of diabetes. The methods of the present invention provide a basis to cost effectively shift the paradigm of treatment to a point in time for those at high (or elevated) risk of developing diabetes related complications prior to actual accumulation of angiopathic damage and downstream resultant complications. Risk and cost appropriate therapeutic regimens can then be implemented to achieve appropriate levels of glycemic control. For example, those identified as being most susceptible to complications could have more stringent goals for glycemic control than is generally achieved (HbA1c<6.0%), by initiating intensive insulin delivery and monitoring systems, pancreatic transplants or the artificial pancreas closer to diabetes onset. These risky goals could be justified by the observation that individuals with blood sugars this close to normal, do not develop diabetic complications irrespective of genetic predisposition.

Early more aggressive treatment of other vascular risk factors, or specialized diets with low levels of AGEs and/or OPs, could also be considered. Considering the high risk profiles of individuals detected with the testing, different guidelines for risk of new therapeutic agents may also be justified. The development of therapeutic approaches that could block offending toxic chemical pathways to delay or arrest complications could also be stimulated by information provided by these methods and subsequent additional studies on the basic biochemical mechanisms and pathways responsible for diabetic complications.

In other embodiments, these individuals could be administered medications that modify the renin-angiotensin system. (See e.g., Mauer, et al., Journal of the Renin-Angiotensin-Aldosterone System, 3:262-269 (2002)), cholesterol and VLDL levels can be initiated. (See e.g., Almuti et al., International Journal of Cardiology, 109(1):7-15 (2006); Degenhardt, et al., Cellular & Molecular Biology, 44(7): 1139-45 (1998); and Rosario, et al., Current Diabetes Reports, 6(6):455-62 (2006)). Alternatively, or in addition, specialized diets with low levels of AGEs or oxidative products (Koschinsky, Proc. Nat. Acad. Sci. USA, 94(12): 6474-6479 (1997)) can be used based on the observed levels of biomarkers of interest measured using the methods of the present invention. Information provided by these studies on basic biochemical mechanisms and pathways responsible for diabetic complications could also stimulate development of therapeutic approaches that could modify offending toxic chemical pathways to delay or arrest DN, DR, and/or CVD.

Examples of drugs that can be used to modify diabetes management based on the subject's risk of developing diabetes related complications (e.g., DN) include, but are not limited to, Metformin. (Beisswenger et al., Diabetes and Metabolism, 29:6S95-6S103 (2003); and Beisswenger, et al., Diabetes, 48:198-202 (1999)); Aminoguanidine (Lo, Amino Acids, 5:172 (1993); Hirsh, J., et al., Carbohyd. Res., 232:125-130 (1992); Brownlee, et al., Diabetes Care, 15(12):1835-43 (1992); and Hammes, et al., Proc. Nat. Acad. Sci., 88:11555-11558 (1991)); and Thiamine and/or Benfotiamine (Hammes, et al., Nature Med., 9(3):294-299 (2003)). Additional drugs, biologics, and agents presently licensed or in development additionally find use in the ameliorative methods of the present invention.

Levels of biomarkers of glycation and oxidative stress are risk factors for the rate of development and progression to advanced diabetic retinopathy (DR) and nephropathy (DN) over time. The effects of biochemical biomarkers of glycation and oxidation on defined outcomes can be assessed using a case-cohort design involving DR, DN and CVD cases and controls. For each selected subject, biological samples (e.g., blood plasma and/or urine) obtained at multiple specified times are employed, for example, but not limited to, DCCT randomization; DCCT one year visit; DCCT closeout (=EDIC baseline); and the Epidemiology of Diabetes Interventions and Complications trial (EDIC) year one. This is contemplated to will provide adequate sample numbers and distribution to be representative of each biomarker of interest.

In one contemplated embodiment, the present methods can be used to assess the risk factors for the progression of microvascular and macrovascular disease in type 1 diabetes. The three primary outcomes are the development of advanced retinopathy; (proliferative diabetic retinopathy ("PDR") detectable via fundus photography or the requirement for pan-retinal photocoagulation (laser), nephropathy; (the development (macro) albuminuria (>300 mg albumin/ 24 h) or end-stage renal disease ("ESRD")); and the occurrence of a cardiovascular disease event. Albumin excretion rate is assessed from a four hour timed measurement of albumin excretion rate annually during DCCT and every other year (half/year) during EDIC. The composite cardiovascular outcome includes fatal or non-fatal myocardial infarction or stroke, ischemic angina, revascularization, or silent MI detected on an annual ECG. Furthermore, a case-control design provides an efficient method to test the above aims for each of the three outcomes (case definitions). However, a simple random sample of controls from among those event-free at the end of the trial would be biased owing to a longer average duration of exposure than the cases. A nested case-control study avoids this bias by randomly sampling controls from among those at risk at the time each selected case is observed. The data is then analyzed using a conditional regression model stratified by case-control set, or equivalently, a like-stratified Cox proportional hazards model. For each outcome, 125 cases with 250 controls will provide 85% power to detect an odds ratio of 1.39 per SD difference at the 0.05 level two-sided. With three separate case definitions, three separate nested case-control sub-studies could require up to 3×375=1125 subjects. Alternately, a case-cohort approach can be employed in which a single baseline randomly sampled "sub-cohort" is selected from the full cohort to provide a basis for controls for each case definition. The efficiency (power) of this design for given case-control sample sizes are equivalent to that of a nested case-control study of the same size. Thus, a case-cohort design that yields approximately 250 controls for each case definition provides excellent power to detect meaningful associations of biomarkers with each of these outcomes.

In one present study, a case-cohort of 350 subjects with a 2:1 ratio of secondary to primary cohort subjects was randomly selected since about twice as many cases of each type occurred in the secondary than primary cohorts. This provided some cases of DR, DN and CVD. Additional cases of each type were selected from the remaining 1091 subjects necessary to obtain at least 125 cases of each type. It was not possible to do so exactly because some subjects who were cases by one criterion were also cases from another. Then, for each case definition, 250 or so controls were sampled. Table 4 provides the numbers of cases and controls within the primary and secondary cohorts, and total that were selected.

TABLE 4

Numbers of Cases and Controls with Primary and Secondary Cohorts

|  | Total | Primary | Secondary |
|---|---|---|---|
| CVD | 381 | 159 | 222 |
| Cases | 127 | 53 | 74 |
| Control | 254 | 106 | 148 |
| PDR | 375 | 108 | 267 |
| Cases | 125 | 27 | 98 |
| Control | 250 | 81 | 169 |
| Albuminuria | 375 | 148 | 227 |
| Cases | 125 | 48 | 77 |
| Control | 250 | 100 | 150 |

Since many cases and controls for one outcome are also cases or controls for another outcome, the total study with three sets of cases and controls comprises a total of only 546 subjects, 200 from the primary prevention cohort and 346 from the secondary intervention cohort. It includes all cases of CVD observed at the time the sample was drawn and random samples of 125 of the DR and DN cases observed at that time. For each of the three case definitions, a modification of the Cox proportional hazards model for case-cohort sampling will be used to assess the relative risk per SD of the biomarkers at each time when added individually to models with and without corresponding longitudinal measures of HbA1c. Preferably, models will also be adjusted for primary/secondary cohort, duration of diabetes on entry and the entry level of HbA1c. Models will be fit using just the baseline levels of a biomarker and then also using the values of the biomarker at the three additional time points as a time dependent covariate. The latter will be used to assess whether the baseline biomarker alone confers additional risk independently of the longitudinal HbA1c.

Additionally, models can also be used to evaluate the effects of the set of biomarkers jointly. Before doing so, collinearity diagnostics will be applied to ensure that there is not a degree of linear dependence (inter-correlation) that leads to variance inflation in the estimates. If so, within each group of related markers, the one with the strongest effects will be employed jointly with those from other groups. A likelihood ratio test will then assess whether the final set of biomarkers contributes significantly to a model that also contains the longitudinal HbA1c values.

IV. Method for Predicting a Patient's Risk of Developing Cardiovascular Disease The present invention also provides methods for determining the risk of or rate of a subject developing cardiovascular disease comprising determining the level of one or more biomarkers of interest including, but not limited to, OPs (e.g., MetSO) and/or AGEs (e.g., CEL) present in a biological sample obtained from the subject. It was surprisingly determined that a subject's levels of MetSO were strongly inversely related to incidence of cardiovascular disease (CVD).

More specifically, using a Cox Proportional Hazards Model, methodology described herein, it was determined that an approximate 20% increase in MetSO (HR=0.58 at EDIC baseline) is indicative of an approximate 42% decrease in CVD outcomes based on risk adjusted covariate modeling (e.g., Age, HbA1c, body mass index [BMI], high density lipoprotein [HDL], low density lipoprotein [LDL], sex, systolic blood pressure [SBP], and/or diastolic blood pressure [DBP]) while an approximate 20% decrease (HR 1.72) in MetSO level is indicative of an approximate 72% increase in CVD risk. Based on additional fully adjusted time dependent models, it was determined that (HR=0.61) an approximate 20% increase in MetSO level is indicative of an approximate 39% decrease in CVD endpoints, while an approximate 20% decrease in MetSO is indicative of an approximate 64% increase in CVD risk.

Using Predictive C-statistic modeling it was determined that adding MetSO also significantly increased the predictive power of the c-statistic from 0.711 to 0.783 ($p<0.001$) when added to the covariates mentioned above. The area under the curve (AUC) as used in these models describes the predictive power of the model and is the probability that a subject who experienced a CVD event has a higher risk score than a subject who has not experienced a CVD event. Using only the traditional cardiovascular disease risk modeling factors only, and thus not considering MetSO levels, the classical probability of predicting CVD related outcomes is approximately 0.711. Accordingly, approximately 71.1% of the time the risk score using the traditional risk factors only is larger in subjects with a CVD event than in subjects without a CVD event. The present invention determined that predictive values in CVD risk modeling can be increased to approximately 78.3% when levels of MetSO are included.

V. Methods of Cardiovascular Disease Care

In any of the methods described herein related to ameliorating, treating, and/or preventing the progression of diabetes associated complications (e.g., diabetic retinopathy and/or diabetic nephropathy, microvascular or macrovascular damage) and/or other cardiovascular diseases and complications, the subject can be administered a therapeutic modality or treatment including lifestyle modifications (e.g., diet and exercise), medical interventions, and/or pharmacological agents.

Non-limiting examples of therapeutic pharmacological agents and treatments related to cardiovascular disease(s) include, but are not limited to, the administration of one of more of the following agents: statins, anti-inflammatory agents, anti-thrombotic agents, anti-coagulants, anti-platelet agents, lipid-reducing agents, direct thrombin inhibitors, glycoprotein IIb/IIIb receptor inhibitors, calcium channel blockers, beta-adrenergic receptor blockers, cyclooxygenase-2 inhibitors, and renin-angiotensin-aldosterone system (RAAS) inhibitors.

Non-limiting examples of lipid-reducing agents that can be used to treat a cardiovascular disease in a subject (alone or in combination with other therapies and pharmacological agents) include: a statin, gemfibrozil, cholystyramine, colestipol, nicotinic acid, and probucol. Statins are molecules that are capable of inhibiting the activity of HMG-CoA reductase. Non-limiting examples of statins that can be administered to a subject having a cardiovascular disease (alone or in combination with other therapies and pharmacological agents) include: atorvastatin, cirivastatin, fluvastatin, lovastatin, pitavastatin, pravastatin, rosuvastatin, and simvastatin. Additional examples of statins and other lipid-reducing agents are known in the art.

Non-limiting examples of anti-inflammatory agents that can be used to treat a cardiovascular disease in a subject (alone or in combination with other therapies and pharmacological agents) include: Alclofenac, Alclometasone Dipropionate, Algestone Acetonide, Alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Deflazacort, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lornoxicam, Loteprednol Etabonate, Meclofenamate Sodium, Meclofenamic Acid, Meclorisone Dibutyrate, Mefenamic Acid, Mesalamine, Meseclazone, Methylprednisolone Suleptanate, Morniflumate, Nabumetone, Naproxen, Naproxen Sodium, Naproxol, Nimazone, Olsalazine Sodium, Orgotein, Orpanoxin, Oxaprozin, Oxyphenbutazone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Salycilates, Sanguinarium Chloride, Seclazone, Sermetacin, Sudoxicam, Sulindac, Suprofen, Talmetacin, Talniflumate, Talosalate, Tebufelone, Tenidap, Tenidap Sodium, Tenoxicam, Tesicam, Tesimide, Tetrydamine, Tiopinac, Tixocortol Pivalate, Tolmetin, Tolmetin Sodium, Triclonide, Triflumidate, Zidometacin, Glucocorticoids, and Zomepirac Sodium. One preferred anti-inflammatory agent is aspirin. Additional examples of anti-inflammatory agents are known in the art.

Non-limiting examples of anti-thrombotic agents that can be used to treat a cardiovascular disease in a subject (alone or in combination with other therapies and pharmacological agents) include: plasminogen proactivator, tissue plasminogen activator, Anisoylated Plasminogen-Streptokinase Activator Complex, Pro-Urokinase, (Pro-UK), rTPA (recombinant alteplase or activase), recombinant Pro-UK, Abbokinase, Eminase, Sreptase Anagrelide Hydrochloride, Bivalirudin, Dalteparin Sodium, Danaparoid Sodium, Dazoxiben Hydrochloride, Efegatran Sulfate, Enoxaparin Sodium, Ifetroban, Ifetroban Sodium, Tinzaparin Sodium, Retaplase, Trifenagrel, Warfarin, and Dextrans. Additional examples of anti-thrombotic agents are known in the art.

Non-limiting examples of anti-coagulants that can be used to treat a cardiovascular disease in a subject (alone or in combination with other therapies and pharmacological agents) include: Ancrod, Anticoagulant Citrate Dextrose Solution, Anticoagulant Citrate Phosphate Dextrose Adenine Solution, Anticoagulant Citrate Phosphate Dextrose Solution, Anticoagulant Heparin Solution, Anticoagulant Sodium Citrate Solution, Ardeparin Sodium, Bivalirudin, Bromindione, Dalteparin Sodium, Desirudin, Dicumarol, Heparin Calcium, Heparin Sodium, Lyapolate Sodium, Nafamostat Mesylate, Phenprocoumon, Tinzaparin Sodium, and Warfarin Sodium. Additional examples of anti-coagulants are known in the art.

Non-limiting examples of anti-platelet agents that can be used to treat a cardiovascular disease in a subject (alone or in combination with other therapies and pharmacological agents) include: Clopridogrel, Sulfinpyrazone, Aspirin, Dipyridamole, Clofibrate, Pyridinol Carbamate, Prostaglandin E, Glucagon, Antiserotonin drugs, Caffeine, Theophyllin Pentoxifyllin, Ticlopidine, and Anagrelide. Additional examples of anti-platelet agents are known in the art.

Non-limiting examples of direct thrombin inhibitors that can be used to treat a cardiovascular disease in a subject (alone or in combination with other therapies and pharmacological agents) include: hirudin, hirugen, hirulog, agatroban, PPACK, and thrombin aptamers. Additional examples of thrombin inhibitors are known in the art.

Non-limiting examples of glycoprotein IIb/IIIb receptor inhibitors that can be used to treat a cardiovascular disease in a subject (alone or in combination with other therapies and pharmacological agents) include: ReoPro (abcixamab), lamifiban, and tirofiban. Additional examples of glycoproteinllb/Illb receptor inhibitors are known in the art.

Non-limiting examples of calcium channel blockers that can be used to treat a cardiovascular disease in a subject (alone or in combination with other therapies and pharmacological agents) include: dihydropyridines, such as nifedipine; phenyl alkyl amines, such as verapamil; and benzothiazepines, such as diltiazem. Additional non-limiting examples of calcium channel blockers include amrinone, amlodipine, bencyclane, felodipine, fendiline, flunarizine, isradipine, nicardipine, nimodipine, perhexilene, gallopamil, tiapamil, tiapamil analogues (such as 1993RO-11-2933), phenytoin, barbiturates, and the peptides dynorphin, omega-conotoxin, and omega-agatoxin, and the like and/or pharmaceutically acceptable salts thereof. Additional examples of calcium channel blockers are known in the art.

Non-limiting examples of beta-adrenergic receptor blockers that can be used to treat a cardiovascular disease in a subject (alone or in combination with other therapies and pharmacological agents) include: atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitril HCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, and 7-(2-hydroxy-3-t-butylaminpropoxy) phthalide. The above beta-adrenergic receptor blockers can be used as isomeric mixtures, or in their respective levorotating or dextrorotating form. Additional examples of beta-adrenergic receptor blockers are known in the art.

Non-limiting examples of cyclooxygenase-2 inhibitors that can be used to treat a cardiovascular disease in a subject (alone or in combination with other therapies and pharmacological agents) include those described in U.S. Pat. Nos. 5,474,995; 5,521,213; 5,536,752; 5,550,142; 5,552,422; 5,604,253; 5,604,260; 5,639,780; 5,677,318; 5,691,374; 5,698,584; 5,710,140; 5,733,909; 5,789,413; 5,817,700; 5,849,943; 5,861,419; 5,922,742; 5,925,631; 5,643,933; 5,474,995; and 5,543,297; WO 95/00501, and WO 95/18799 (each of which is incorporated herein by reference). Additional examples of cyclooxygenase-2 inhibitors are known in the art.

Renin-angiotensin-aldosterone system (RAAS) inhibitors can be used to treat a cardiovascular disease in a subject (alone or in combination with other therapies and pharmacological agents) include agents that interfere with the function and synthesis or catabolism of angiotensin II. RAAS agents include, but are not limited to, angiotensin-converting enzyme (ACE) inhibitors, angiotensin II receptor blockers, agents that activate the catabolism of angiotensin II, agents that prevent the synthesis of angiotensin I (from which angiotensin II is ultimately derived), and aldosterone antagonists. The RAAS is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function. RAAS inhibitors are compounds that act to interfere with the production of angiotensin II from angiotensinogen or angiotensin I or interfere with the activity of angiotensin II. Such inhibitors are well known in the art and include compounds that act to inhibit the enzymes involved in the ultimate production of angiotensin II, including renin and ACE. They also include compounds that interfere with the activity of angiotensin II, once produced.

Angiotensin II receptor blockers include angiotensin II antagonists which interfere with the activity of angiotensin II by binding to angiotensin II receptors and interfere with their activity. Angiotensin II receptor blockers are well known and include peptide compounds and non-peptide compounds. Most angiotensin II receptor blockers are slightly modified congeners in which agonist activity is attenuated by replacement of phenylalanine in position 8 with some other amino acid. Examples of angiotensin II receptor blockers include: peptidic compounds (e.g., saralasin, [(San1)(Val5)(Ala8)] angiotensin-(1-8) octapeptide, and related analogs); N-substituted imidazole-2-one (U.S. Pat. No. 5,087,634); imidazole acetate derivatives, including 2-N-butyl-4-chloro-1-(2-chlorobenzile), imidazole-5-acetic acid (see, Long et al., J. Pharmacol. Exp. Ther. 247:1-7, 1988); 4,5,6,7-tetrahydro-1H-imidazo [4,5-c] pyridine-6-carboxylic acid, and analog derivatives thereof (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives, such as 1, 3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds, such as biphenyl-methyl substituted imidazoles (e.g., EP 253,310); N-morpholinoacetyl-(-1-naphthyl)-L-alanyl-(4, thiazoyl)-L-alanyl (35, 45)-4-amino-3-hydroxy-5-cyclo-hexapentanoyl-N-hexylamide; SKF108566 (E-alpha-2[2-butyl-1-(carboxyphenyl)methyl] 1H-imidazole-5-yl[methylane]-2-thiophenepropanoic acid); Losartan; Remikirin; and A2 agonists.

Non-limiting examples of ACE inhibitors include acyl-mercapto and mercaptoalkanoyl prolines, such as captopril (U.S. Pat. No. 4,105,776) and zofenopril (U.S. Pat. No. 4,316,906); carboxyalkyl dipeptides, such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729); carboxyalkyl dipeptide mimics, such as cilazapril (U.S. Pat. No. 4,512,924) and benazapril (U.S. Pat. No. 4,410,520); and phosphinylalkanoyl prolines, such as fosinopril (U.S. Pat. No. 4,337,201) and trandolopril.

Additional non-limiting examples of RAAS inhibitors include: derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine, or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437) (each of which is incorporated by reference).

Additional examples of RAAS inhibitors include aldosterone antagonists. Non-limiting examples of aldosterone antagonists include: Spironolactone, Eplerenone, Canrenone (canrenoate potassium), Prorenone (prorenoate potassium), and Mexrenone (mexrenoate potassium).

The present invention will be further understood by reference to the following non-limiting examples.

Example 1

The Relationship Between Plasma Levels of AGEs and OPs and Nephropathy Progression/Non-Progression Instrumentation: HPLC—Agilent 1200 Series Binary Pump, Autosampler, Degasser and Thermostatted Column Chamber; QQQ—Agilent 6410.

Materials: MS grade water and methanol are from Honeywell (Honeywell, USA). Heptafluorobutyric acid (HFBA) LC grade, Fisher, (Pierce Chemical) #PI-53104. HPLC Column-Gemini-NX 3 u C18, 4.6 mm×250 mm Phenomenex #00G-4453-E0.

Since the analysis of 9 proposed biomarkers by LC-MS/MS is done on a single run, and requires the addition of heavy isotope internal standards for accurate quantification, the required light and heavy standards for nine biomarkers were obtained as follows: Light and heavy ($N^{15}$) 3DG-HI was obtained from Organix (Essex, UK). Heavy MG-H1 and G-HI, was produced by NeoMPS (Strasbourg, France). Methionine sulfoxide and dityrosine were synthesized, and light and heavy standards of the remaining 5 biomarkers (Pentosidine, CEL, CML, MG-H1 and GH) were purchased from available commercial sources. 2-Aminoadipic Acid, a stable lysine derived end product which is an excellent indicator of oxidative stress was obtained from Sell and Monnier at Case Western Reserve University in Cleveland Ohio (Beisswenger, et al., Diabetes, 54:3274-3281 (2005)). The addition of heavy isotope internal standards for accurate quantification is required since the analysis of these 9 proposed biomarkers by LC-MS/MS is done on a single run.

Measurement of Biomarkers: The methods developed for the concurrent quantitative measurement of biomarkers indicative of protein glycation, oxidation, and nitrosative damage (Ahmed, et al., Biochemical Journal, 364(Pt 1): 1-14 (2002) were modified by employing a single 2.0×250 mm Synergy 4 micron 80A column (Phenomenex) with a mobile phase of Methanol/$H_2O$ gradient with concentration of 0.29% heptafluorobutyric acid on the Agilent Model 1200 HPLC, with a total analysis time of 60 min on an Agilent Model 6410 triple quadrupole Mass Spectrometer (QQQ), and approach not used in the art in measuring AGEs or oxidation products.

A novel change in this protocol relative to known methods for measuring AGEs is the completely different stationary phase used i.e., C18 (e.g., the Synergy 4 micron 80A column). This column change resulted in use of mobile phase conditions which differ from prior art methods i.e., the use of heptafluorobutyric acid as an ion pairing agent. The combination of column type and mobile phase also allowed the sample analysis to be performed with a single column relative as opposed requiring 2 columns i.e., samples could successfully be run using one column—two columns were not required. The HPLC and QQQ conditions are shown below.

HPLC Conditions, Mobile Phase: Solvent A=95% 0.29% HFBA in water/5% 0.29% HFBA in methanol. Solvent B=0.29% HFBA in methanol. Flow rate=0.25 ml/min Pump Time. (Table 5).

TABLE 5

| Time | Solvent Ratio B |
|---|---|
| 0 | 0 |
| 3 | 0 |
| 25 | 29 |
| 35 | 100 |
| 45 | 100 |
| 50 | 0 |
| ... | ... |
| 70 | 0 |

Column Temperature: 28° C.

QQQ Acquisition Parameters: The Agilent 6410 MS/MS, equipped with an ESI source was operating in the positive mode under the following conditions: Drying gas was at 350 C with a flowrate of 10 L/min. Nebulizer pressure was 40 psi and capillary voltage was set for 4000 for all compounds. Detailed compound analytical parameters are shown in Table 6. Using isotopic dilution analysis quantitation of samples was achieved by reading from calibration curves derived from relative response vs. relative concentration to the heavy standard. Heavy standards were added to plasma or urine filtrates at final concentrations from 1 to 6 uM in concordance with the expected physiological concentrations and range of the standard curves. The order of elution of the compounds is as shown in Table 7 This table also shows the coefficient of variation (COV) for repeated between day measurements of the analytes, as well as the lower limit of detection (LLOD) and lower limit of Quantitation (LLOQ) for each analyte.

TABLE 6

Compound Analytical Parameters for Mass Spectrometry

| Compound[1] | Transition | Fragmentor V | Collision V |
|---|---|---|---|
| CML (Quantifier)[2] | 205.1-84.1 | 100 | 22 |
| CML (Qualifier)[2] | 205.1-130.1 | 100 | 8 |
| d4 CML (Isotope)[2] | 209.1-88.1 | 100 | 22 |
| CEL | 219.1-84.1 | 100 | 22 |
| CEL | 219.1-130.1 | 100 | 8 |
| d4 CEL | 223.1-88.1 | 100 | 22 |
| MetS0 | 166.1-74.1 | 80 | 7 |
| MetS0 | 166.1-102.1 | 80 | 10 |
| d3 MetS0 | 169.1-74.1 | 80 | 7 |
| 3-NT | 227-181 | 94 | 8 |
| 3-NT | 227-117 | 94 | 20 |
| 6C[13] 3-NT | 233-187 | 94 | 8 |
| MG-H1 | 229-166.1 | 104 | 13 |
| MG-H1 | 229-114 | 87 | 12 |
| d3 MG-H1 | 232.1-169.2 | 104 | 13 |
| MG-H2 | 229-116 | 87 | 12 |
| MG-H2 | 229-114 | 87 | 12 |
| d3 MG-H1 | 232.1-169.2 | 104 | 13 |
| MG-H3 | 229-114.1 | 87 | 12 |
| MG-H3 | 229-116 | 87 | 12 |
| d3 MG-H1 | 232.1-169.2 | 104 | 13 |
| DiTyr | 361.1-315.1 | 100 | 10 |
| DiTyr | 361.1-254.1 | 100 | 18 |
| 2C[13] DiTyr | 363.1-316.1 | 118 | 12 |
| G-H1 | 215-152 | 80 | 9 |
| G-H1 | 215-116 | 80 | 5 |
| 2C[13] G-H1 | 217.2-154.1 | 104 | 12 |
| G-H2 | 215.1-116.1 | 80 | 5 |
| G-H2 | 215.1-100.1 | 100 | 10 |
| 2C[13] G-H1 | 217.2-154.1 | 104 | 12 |
| G-H3 | 215.1-100.1 | 100 | 10 |
| G-H3 | 215.1-116.1 | 80 | 5 |
| 2C[13] G-H1 | 217.2-154.1 | 104 | 12 |
| 3DG-H | 319.1-204.2 | 120 | 14 |
| 3DG-H | 319.1-116.1 | 120 | 22 |
| 6C[13]4N[15] 3DG-H | 329.1-208.1 | 120 | 14 |
| AAA | 162.2-98.1 | 52 | 12 |
| AAA | 162.2-144.2 | 52 | 4 |
| d3 AAA | 165.2-101.2 | 55 | 12 |

[1]Capillary voltage was set at 4000 for all transitions
[2]Transitions remain in the same order throughout table

TABLE 7

Validation of Analytical Method

| Compound | Mean(nM)[1] | Between day COV %[1] | LLOD[2] (nM) | LLOQ[2] (nM) |
|---|---|---|---|---|
| MetSO | 1610 | 11.2 | 64 | 210 |
| AAA | 1380 | 9.6 | 81 | 270 |
| CML | 110 | 10.1 | 10 | 34 |
| CEL | 62 | 10 | 8.6 | 28 |
| 3DG-H | 450 | 10.9 | 40 | 130 |
| G-H1 | 22 | 11.6 | 3.1 | 10 |
| MG-H1 | 303 | 8.6 | 5.8 | 19 |
| 3-NT | <LLOQ | — | 2.2 | 7.1 |
| DiTyr | <LLOQ | — | 2.9 | 9.5 |

[1]Calculated from replicate injections of a pooled plasma filtrate n = 218
[2]Calculated from the standard deviation of the response (SD) and the slope (S) of calibration curves.
LLOD = 3.3(SD/S) LLOQ = 10(SD/S) Values represent the mean of five calibration curves.
$R^2$ value exceeds 0.99 for all calibration curves Source Parameters: Mode: ESI Positive Gas Temp. (350° C.)

Methods for Sample Preparation: Plasma sample preparation: All of the samples used in this study were collected at the 5-year end of study NHS visit by a rigorous protocol, where blood was collected in EDTA containing tubes and immediately iced and centrifuged. Following centrifugation plasma was immediately separated from red blood cells (RBCs) and snap-frozen on dry ice, and subsequently stored at −80° C. until these analyses were performed.

Ultrafiltrates (free adducts): LC-MS/MS analyses were initially performed on the plasma "free fraction," prepared as the filtrate following centrifugation through 10K cut-off Amicon filters (EMD Millipore Corp., Billerica, Mass.).

Adduct residues chemically bound to plasma proteins: Since some of the products are acid labile, chemically bound products are determined after exhaustive sequential enzymatic digests with pepsin, Pronase E, and Aminopeptidase/ prolidase (50 μg protein equivalent) under nitrogen, with controls for protease autolysis, as described by Ahmed, et al., Biochem J., 364(Pt 1):1-14(2002). AGE/OP analyses were performed following extensive sequential plasma digestion over 36 hours with 3 proteolytic enzymes under a nitrogen atmosphere (Ahmed, et al., Diabetologia, 48:1590-1603 (2005)) to investigate the protein "bound" fraction.

Urine sample Preparation: For analysis of the biomarkers in urine, 4 samples per subject distributed over the 5 year NHS study, were tested.

Preparation of urine samples to measure excretion of adducts: For determination of the AGE and OP biomarker profile in urine, a filtrate prepared by centrifugation at 4° C. through microspin filters (10,000 MW filter cut-off) as described by Ahmed, et al., Diabetologia, 48:1590-1603 (2005) were used. Urine creatinine levels can be determined to provide uniform expression of pro duct/creatinine urine analyte content.

LC-MS/MS was performed on the NHS urine samples which provided an initial total population of 107 subjects consisting of nephropathy progressors (n=37), and non-progressors (n=70). The studies were completed (220 (55×4) additional analyses) over a 10-week period, utilizing a throughput of 24 samples per week. The statistical tests were done on the full sample (n=107 subjects) with a two-sided alpha=0.01. The assumption was that the SD in the whole study sample is the same as the sub-sample (N=52). The urinary and serum "free fraction" determinations also allow the calculation of renal clearance rates of each analyte.

Results

A. Plasma Filtrates (Free Fraction)

Since it is the best early structural predictor of DN clinical progression in this type 1 diabetes population, change in glomerular basement membrane (GBM) width from baseline to 5 years in the NHS population measured in electron micrographs of renal biopsies, was the primary endpoint. Mesangial fractional volume was also measured. Fast progressors (FP) were defined as the upper quartile (n=24) of GBM thickening and others as slow progressors (SP). AGEs (3-deoxyglucosone and methylglyoxal hydroimidazolones (DG3H1, MG-H1)) and carboxymethyl and ethyl lysine (CML, CEL), and oxidation products (methionine sulfoxide and 2 Aminoadipic Acid) were measured by liquid chromatography, triple quadruple mass spectroscopy on 10 K plasma filtrates on 102 samples at year 5. It was found that MG-H1, CEL, and CML levels were significantly higher in GBM-defined FP relative to SP. No AGE or OP predicted mesangial expansion in these studies.

Figure 3:
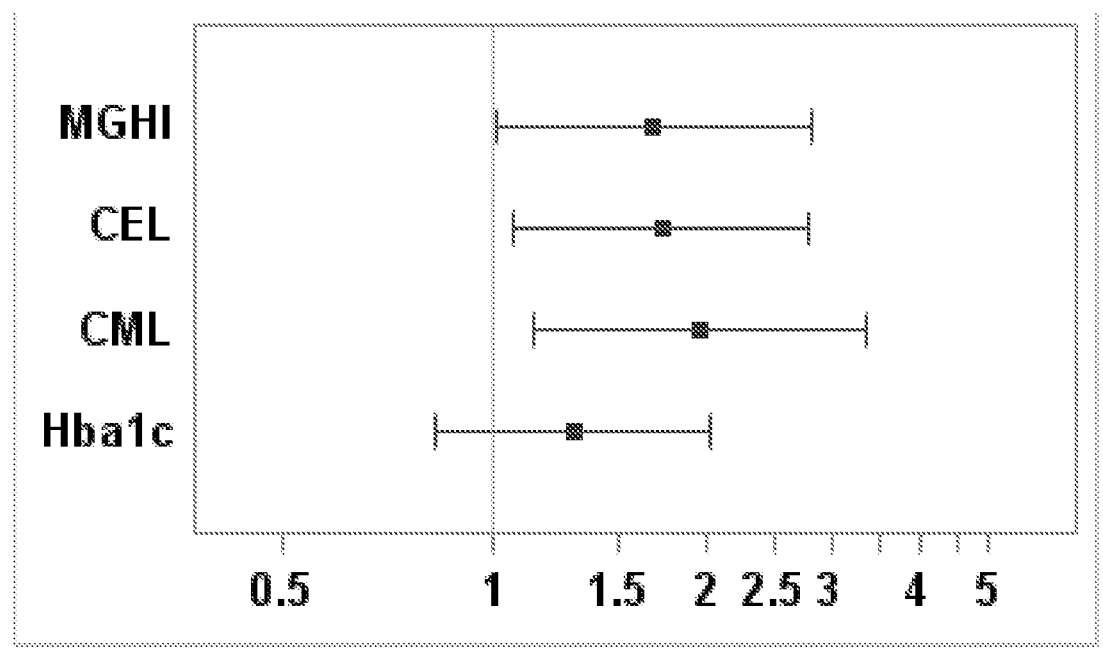
FIG. 3 is a forest plot of the odds ratios (and 95% confidence intervals) for a one standard deviation change in the three informative biomarkers (CML, CEL, and MG-H1), and HbA1c, as calculated from the logistic regression model. For example, a one SD increase in CEL would lead to a 1.72 increase in the odds of being in the fast progression group. The p values for these plots are associated with those shown in FIGS. 2A-D.
Figure 4A:
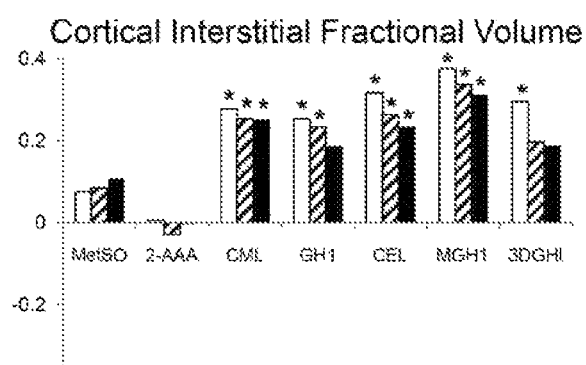
FIGS. 4A, 4B, 4C, and 4D show, respectively, cortical interstitial fractional volume (4A); fractional Mesangial volume (4B); Global glomerular sclerosis (4C); and total filtration surface (4D).
Figure 4B:
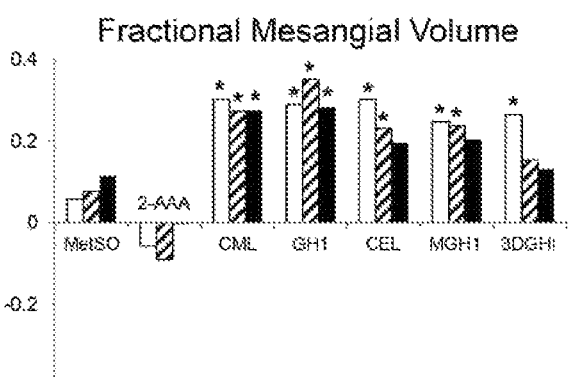
Figure 4C:
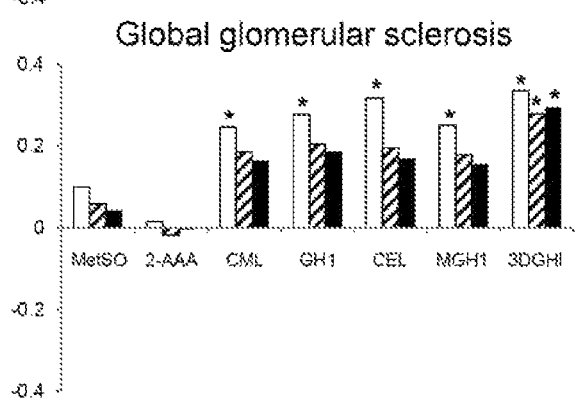
Figure 4D:
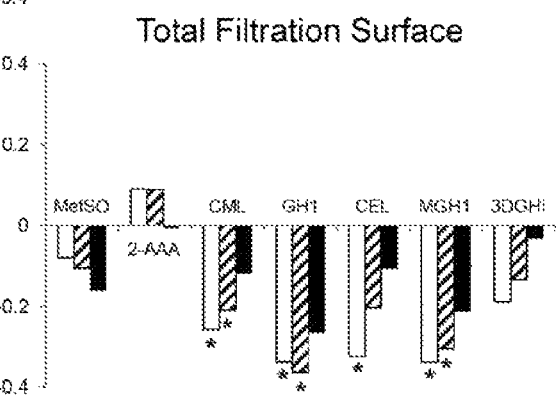
Figures 5A, 5B:
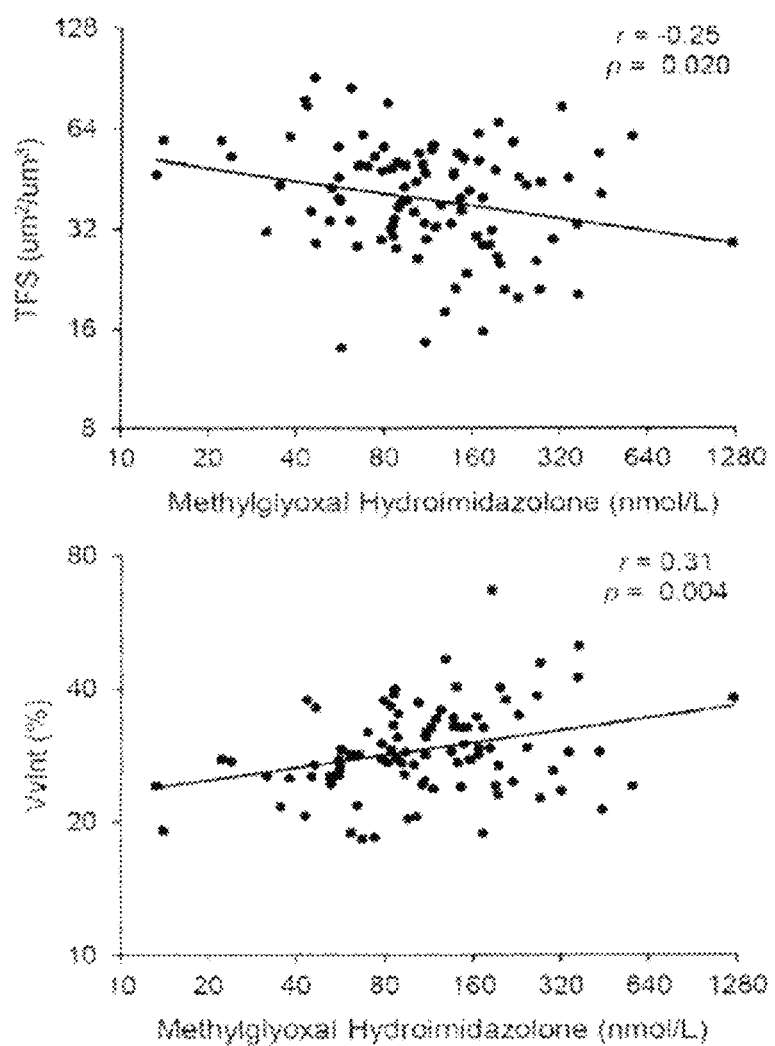
FIGS. 5B and 5B show MGH1 and fractional cortical interstitial volume, respectively.

These results show three AGEs (Table 8; FIG. 3), as early indicators of progression of clinically relevant DN lesions. The other AGE and oxidative biomarkers measured in this study did not correlate with DN progression (Table 7).

TABLE 8

Plasma Biomarker Levels in Fast and Slow Nephropathy Progressors: Based on Rates of GBM Thickening Over 5 Years

| Biomarker (All nM) | Fast Mean ± SD | Slow Mean ± SD | P- Value Wilcoxon | Number Progressors/Non-Progressors |
|---|---|---|---|---|
| CML | 0.088 ± 0.022 | 0.075 ± 0.023 | 0.003* | 22/79 |
| GHI | 0.013 ± 0.001 | 0.013 ± 0.002 | 0.16 | 22/79 |
| MG-H1 | 0.200 ± 0.099 | 0.165 ± 0.127 | 0.04* | 22/79 |
| CEL | 0.058 ± 0.015 | 0.049 ± 0.015 | 0.026* | 22/79 |
| 3DGHI | 0.382 ± 0.154 | 0.330 ± 0.156 | 0.28 | 22/79 |
| MetSO | 0.931 ± 0.304 | 0.979 ± 0.348 | 0.97 | 22/79 |

Further analyses supporting the value of these three biomarkers in predicting early diabetic nephropathy are the observations that HbA1c at year 5 accounted for 4.7% of the variation in GBM width ($R^2$), but the proportion of variation in GBM width accounted for was increased to 11.6% when MG-H1, CEL, and CML were added to the model (7.9% increase). Further, these analyses revealed MG-H1 as a significant independent predictor of GBM increase.

These findings indicate that MG-H1, CEL, and CML are consistently low in those who are protected from progression; thus the biomarkers should identify those protected from DN. The ordered data for MG-H1 shows that 2 of 31 (6% of lower tertile) MG-H1 values of fast nephropathy progressors are in the bottom 30% (31 of 103) of the ordered values, but MG-H1 values of 29 of 31 (94%) slow nephropathy progressors make up this bottom 30%. This was also true of the findings for CEL and CML, where 30 of 32 (94%) of the lowest values were seen in slow progressors for both biomarkers. The levels of these 3 biomarkers were also compared to previously obtained levels for Non-progressors. (Ahmed, et al., Diabetologia, 48:1590-1603 (2005); and Ahmed, et al., Science, 44(12):5287-92 (2003)). As shown in Table 9 these studies show that the mean levels for the protected group (DN non-progressors) are similar or slightly higher than levels seen in non-diabetic controls.

TABLE 9

AGEs in Diabetics Compared to Non Diabetic Subjects

|  | CML | CEL | MG-H1 |
|---|---|---|---|
| #Type 1 diabetes n = 106 | 78 | 51 | 172 |
| ‡Type 1 diabetes n = 21 | 97 | 72 | 331 |
| * Non-diabetic Subjects. N = 6 | 23 | 35 | 110 |
| ‡Non diabetic Subjects Lower Tertile of DN progression n = 32 | 27 | 25 | 43 |
|  | 52.4 ± 7.5 | 34.5 ± 6.1 | 71.9 ± 23.2 |

Data from present study
* Data from Ahmed, Biochem Soc Trans, 31(Pt 6): 1417-22 (2003)
‡Data from Ahmed, et al., Diabetologia, 48: 1590-1603 (2005)

The results show that in some embodiments the level of three AGEs in plasma filtrates (but no OPs), alone or in addition to HbA1c combination, that the three major AGEs, are clinically relevant predictors (in addition to HbA1c in some instances) of progression to DN.

B. Results on Biomarkers in Extensively Digested Plasma Samples to Investigate their Relationship with Progression of DN Similar statistical analyses were performed to determine if AGEs and OP (measured on extensive plasma digests of 102 samples, performed as described by Ahmed, et al., Diabetologia, 48:1590-1603 (2005), show any correlation with progression of DN defined by GBM thickening or mesangial expansion. Fast progressors (FP) were defined as the upper quartile (n=24) of GBM thickening and the remainder as slow progressors (SP). The same products were measured as performed on the "plasma filtrate" except for 2-Aminoadipic Acid (AAA) which was not measurable on digests, and GHI which was below the limits of detectability. (See, Table 7). As shown in Table 10 below, there was no correlation between levels of biomarkers in plasma digests and progression of DN.

TABLE 10

Statistical Data for Levels of Biomarkers in Plasma Digest

|  | t-test | Wilcoxon |
|---|---|---|
| CML | 0.62 | 0.75 |
| MetS0 | 0.28 | 0.36 |
| 3DG-H1 | 0.61 | 0.50 |
| CEL | 0.70 | 0.61 |
| MG-H1 | 0.22 | 0.30 |

The degree of elevation in protein bound AGEs and OPs were modest, relative to that seen in either plasma of urinary "free" fractions, suggesting less modification of relatively short half-life plasma proteins in diabetes. See, Table 11.

TABLE 11

Plasma Hydrolysates Biomarker Levels in
Plasma in type 1 Diabetes and Controls

|  | CML | MetSO | 3DG-H | CEL | G-H1 | MG-H1 |
|---|---|---|---|---|---|---|
| DMS NHS samples (Type 1 Diabetes) | 0.031 | 12.8 | 1.03 | 0.0019 |  | 0.024 |
| DMS normal controls n = 8 | 0.024 | 9.94 | 0.93 | 0.0011 |  | 0.022 |

Values expressed as mean mmoles/mole AA

The data in Table 12 shows that none of these protein-bound AGE or OP biomarkers in plasma were related to nephropathy progression or non-progression, based on the degree of GBM change or MES change.

C. Results from Completion of Analysis of Urinary AGEs and Oxidation Products

For these studies, fast progressors (FP) were defined as the upper 37 subjects with the greatest degree of GBM thickening and slow progressors (SP) as the remainder. The analyses were done on the dataset that was corrected for a few outliers where a value was excluded if it was >2 SD beyond that person's own individual mean. The mean values for the 8 measured biomarkers by Progressor (fast)/Non-Progressor (slow) are shown in Table 12. Of those 8, only urinary levels of CEL (p=0.04) showed a significant difference between groups. CML is next closest (p=0.10), then DiTyr (p=0.16), with all other p-values>0.25. To further confirm these results, the analyses were repeated using non-parametric methods (Wilcoxon Rank-Sum Test), and only CEL (p=0.02) was different between groups. No biomarker correlated with the degree of mesangial expansion over 5 years.

TABLE 12

Urinary Biomarker Levels in Nephropathy Progressors
(Fast) and Non-Progressors (Slow)

| grp | N Obs | N | Mean | Std Dev | Minimum | Maximum |
|---|---|---|---|---|---|---|
| Analysis Variable: gh1 ||||||||
| fast | 35 | 35 | 1.35 | 0.63 | 0.76 | 4.20 |
| slow | 89 | 89 | 1.30 | 0.47 | 0.59 | 3.10 |
| Analysis Variable: dityr ||||||||
| fast | 35 | 34 | 0.058 | 0.012 | 0.042 | 0.093 |
| slow | 89 | 89 | 0.055 | 0.013 | 0.036 | 0.100 |
| Analysis Variable: mgh1 ||||||||
| fast | 35 | 35 | 41.4 | 17.6 | 19.2 | 89.4 |
| slow | 89 | 89 | 38.7 | 19.3 | 10.8 | 100.9 |
| Analysis Variable: aaa ||||||||
| fast | 35 | 35 | 96.9 | 46.9 | 30.9 | 208.5 |
| slow | 89 | 89 | 93.8 | 53.5 | 17.9 | 400.1 |
| Analysis Variable: cml ||||||||
| fast | 35 | 35 | 15.1 | 5.4 | 8.3 | 25.7 |
| slow | 89 | 88 | 13.3 | 5.5 | 5.7 | 30.8 |
| Analysis Variable: methso ||||||||
| fast | 35 | 35 | 5.54 | 4.09 | 1.23 | 16.43 |
| slow | 89 | 89 | 5.09 | 3.36 | 0.65 | 15.01 |
| Analysis Variable: dgh3 ||||||||
| fast | 35 | 35 | 51.2 | 18.5 | 23.5 | 89.5 |
| slow | 89 | 89 | 47.5 | 21.9 | 20.2 | 164.2 |
| Analysis Variable: cel ||||||||
| fast | 35 | 35 | 7.29 | 1.83 | 3.99 | 11.65 |
| slow | 89 | 88 | 6.46 | 2.05 | 2.83 | 13.14 |

Although statistical significance was obtained with CEL, when these results were adjusted for other variables know to effect DN progression, (gender, diabetes duration, age, and HbA1c), these correlations between CEL and DN Progression/Non-Progression were no longer statistically significant (Table 13).

TABLE 13

Univariate and Multivariate Analysis
of CEL in Urine and GBM Thickening

|  | CEL ||
|---|---|---|
|  | Beta | p-values |
| single var (GBM, age adj) |  |  |
| Biomarker (CEL) | 1.17 | 0.039 |
| multivariate (GBM, age adj) |  |  |
| Biomarker (CEL) | -0.118 | 0.82 |
| HbA1c | 4.43 | <0.0001 |
| Duration | -1.15 | <0.0001 |
| Gender (if F) | -6.45 | 0.0033 |

These outcomes indicate that carefully quantified, specific urinary AGEs and Oxidative biomarkers do not show a statistically significant independent relationship with progression of biopsy proven diabetic nephropathy.

Example 2

Association Between Serum AGE Concentrations
with Loss of Renal Function and Structural Lesions
on Kidney Biopsies Type 2 Diabetes Patients The present Example describes the association between serum AGE concentrations with loss of renal function and structural lesions on kidney biopsies in Pima Indians with type 2 diabetes and early DN. These studies of specific end-products confirm a role for elevated methylglyoxal levels in the development of diabetic nephropathy in type 2 diabetes and confirm prior findings focused on type 1 diabetes. The role of these specific AGE biomarkers in progression of diabetic nephropathy was confirmed by demonstrating correlations with clinical outcomes and their related morphological renal changes (Table 19).

Column Selection: based on the unsatisfactory outcomes achieved with the porous shell technologies, preferred embodiments, as described herein and presented in the instant Example, returned to investigations with C18 RP column technologies and ion pairing agents (e.g., heptafluorobutyric acid). Accordingly, a number of LC columns were investigated including: Synergi Hydro-RP®, 4 μm, 2.0×250 mm (Phenomenex, Inc.); Gemini-NX® C18, 3 µm, 2.0×250 mm ((Phenomenex, Inc.); Thermo: Accupore Polar Premier®, 2.6 µm, 2.1×150 mm (Thermo Fisher Scientific, Tewksbury, Mass.); and Waters X-Select®, 2.5 µm, 2.1×150 mm (Waters Corp., Milford, Mass.). Extensive testing led to selection of the Waters X-select stationary phase, in preferred embodiments, as providing optimal balance of desired characteristics. This column is sufficiently retentivity for MetSO, to aide in ion suppression interests while maintaining the required selectivity to perform chromatographic separations. Therefore, this column was chosen for further validation.

The column was further tested using standard curve and IS solutions prepared based on the information obtained from preliminary work with the Waters X-select column. The reproducibility over the concentration range and linearity of the standard curve allowed further evaluations (e.g., into ion suppression). The column adequately alleviated ion suppression interest associated with MetSO. Further instrumentation details developed for one embodiment of the Agilent 6490 LC/MS/MS acquisition utilizing the column and associated methodologies are detailed in Tables 14, 15, and 16.

TABLE 14

| Agilent 6490 MS/MS | |
| --- | --- |
| Product Specifications | 2-1290 Series Binary Pumps Thermostated 1290 series Autosampler 1316C Column Compartment |
| Mass Spectrometer Parameters | Ion source Scan Type AJS ESI Delta EMV Start time Dynamic MRM 500 Polarity 3.2 mins Positive |
| Source Parameters | Gas Temp C. Gas Flow 220 L/min Nebulizer (psi) 18 Sheath Gas C Sheath 35 Gas Flow Capillary V 400 Vcharging 12 3000 0 |
| Ion Funnel Parameters | Pos High Pressure RF 130 Pos Low Pressure RF 50 |
| LC Configuration | Columns: 2- Waters X-select HSS T3 2.5 um x 2.1 x 150 mm Mobile phase A 0.2% HFBA in water Mobile phase B 0.2% HFBA in methanol |

Two binary pumps were configured to make an analytical run with one pump while simultaneously re-equilibrating the other column with the other pump, thereby allowing for un-interrupted analytical runs. Details of this chromatographic configuration are located in Table 15 and Table 16.

TABLE 15

| Binary Pump 2 Configured Analytical Pump with Constant Flow Rate | | |
| --- | --- | --- |
| Time | Flow Rate | Solvent composition |
| 0 | 0.26 ml/min | 95% A-5% B |
| 4.5 | | 95% A-5% B |
| 5.0 | | 75% A-25% B |
| 13.0 | | 65% A-35% B |
| 16 | | 0% A-100% B |
| 18 | | 0% A-100% |
| 18.01 | | 95% A-5% B |
| 19 Stop time | | |

TABLE 16

| Binary Pump 1 Configured as Re-Equilibration Pump | | |
| --- | --- | --- |
| Time | Flow Rate | Solvent composition |
| 0 | 0.26 ml/min | 95% A-5% B |
| 0.01 | 0.10 ml/min | 95% A-5% B |
| 9 | 0.10 ml/min | 95% A-5% B |
| 9.01 | 0.26 ml/min | 95% A-5% B |
| 19 Stop Time | | |

1290 Series Auto Sampler Configuration: Temperature 4° C.; Injection volume 1 µl; 1316C Column Compartment Configuration: Temperature 24° C.; Injection port valve set to switch position at the end of every run.

Qualitative and Quantitative evaluation of standards were additionally performed to optimize the precision and reproducibility of our method.

Liquid Chromatography/Triple Quadrupole Mass Spectroscopy: Liquid Chromatography/Triple Quadrupole Mass Spectroscopy (LC-MS/MS) was used to measure the profile of 9 unique biomarkers (i.e., 5 Advanced Glycation End-products (AGEs): $N_\varepsilon$-Carboxymethyl Lysine (CML), $N_\varepsilon$-Carboxyethyl Lysine CEL, Glyoxal Hydroimidazolone (G-H1), Methylglyoxal Hydroimidazolone (MG-H1); and 3-Deoxyglucosone Hydroimidazolone (3-DGH); and four oxidation end products: Methionine Sulfoxide (MetSO); 3-Nitrotyrosine (3-NT), 2-Aminoadipic Acid (AAA); and Dityrosine (DiTyr)) utilizing internal standardization by stable heavy isotope substituted standards.

Serum samples from fasting patients were collected at baseline by a carefully defined rapid separation and snap freezing protocol and stored at −80° C. for analysis of the biomarkers of interest. Analyses were performed on the free fraction, prepared as the filtrate following centrifugation through 10K cut-off Amicon filters.

Table 17 provides Clinical Characteristics of Study Population at Baseline and Time of Renal Biopsy. The study population included patients from Pima Native Americans with type 2 diabetes and no DN or early DN (See, ClinicalTrials.gov number, NCT00340678). All additional morphological, biochemical and histological data provided in the instant Example was obtained from the above-mentioned Pima Native American type 2 diabetes trial.

TABLE 17

| Clinical Characteristics of Study Population at Baseline and Time of Renal Biopsy | | | |
| --- | --- | --- | --- |
| Characteristic | Full Cohort, Baseline n = 168 Mean ± SD | Biopsy Cohort, Baseline n = 106 Mean ± SD | Biopsy Cohort, Biopsy n = 106 Mean ± SD |
| Clinical Measures | | | |
| Age (years) | 41.4 ± 10.6 | 40.3 ± 9.9 | 45.9 ± 9.8 |
| Sex (male, %) | 46 (27%) | 28 (26%) | — |
| Diabetes Duration (years) | 8.9 (6.2-14.9) | 8.8 (6.1-14.1) | 14.2 (11.7-20.2) |
| BMI (kg/m$^2$) | 35.7 ± 8.4 | 35.2 ± 8.0 | 35.8 ± 7.9 |
| Systolic Blood Pressure (mmHg) | 118 ±13 | 117 ± 13 | 124 ± 15 |
| Diastolic Blood Pressure (mmHg) | 75 ± 6 | 75 ± 7 | 78 ± 9 |
| Fasting Plasma Glucose (mg/dL) | 194 ± 79 | 200 ± 79 | 205 ± 91 |
| HbA1c (%) | 9.2 ± 2.3 | 9.3 ± 2.3 | 9.3 ± 2.1 |
| ACR (mg/g) | 30.6 (13.5-76.3) | 29. 5 (12.1-66.0) | 38.2 (13.5-158.3) |

TABLE 17-continued

Clinical Characteristics of Study Population at Baseline and Time of Renal Biopsy

| Characteristic | Full Cohort, Baseline n = 168 Mean ± SD | Biopsy Cohort, Baseline n = 106 Mean ± SD | Biopsy Cohort, Biopsy n = 106 Mean ± SD |
|---|---|---|---|
| Serum Creatinine (mg/dL) | 0.68 ± 0.16 | 0.68 ± 0.16 | 0.73 ± 0.22 |
| GFR (ml/min) | 164.0 ± 41.7 | 162.7 ± 39.6 | 145.9 ± 56.4 |

AGEs and oxidation end-products were measured once at baseline in 168 subjects and in 106 of those individuals who went on to have a renal biopsy, and Table 18 describes the biochemical characteristics of Pima Native American study subjects.

TABLE 18

Biochemical Characteristics of Pima Native American Study Subjects' AGEs and oxidation end-products

| AGEs and OPs | All subjects at Baseline (n = 168) nmols/L Mean (range) | Subjects with Biopsy (n = 106) nmols/L Mean (range) |
|---|---|---|
| MetSo | 683.6 (581.2-803.4) | 662.2 (566.6-776.2) |
| AAA | 861.7 (659.1-1097.7) | 883.9 (680.1-1067.5) |
| Carboxymethyl Lysine | 59.0 (45.9-74.1) | 58.8 (44.1-73.9) |
| 3-DG Hydroimidazolone | 193.5 (160.2-290.4) | 191.6 (160.5-271.1) |
| Carboxyethyl Lysine | 45.3 (35.2-57.6) | 45.6 (35.0-57.6) |
| Glyoxal Hydroimidazolones | 7.3 (6.5-8.6) | 7.3 (6.4-8.5) |

Table 19 presents morphometric measurement data on renal biopsies performed on study participants 6 years following entry into the Pima Native American type 2 diabetes study.

TABLE 19

Morphometric Measures on Renal Biopsy Performed 6 Years Following Study Entry

| Measure | Mean (range) |
|---|---|
| GBM width (nm) | 502 (419-594) |
| Mesangial fractional volume (%) (VvMes) | 18.3 (14.1-24.9) |
| Total filtration surface per glomerulus (×$10^5$ $\mu^2$) | 4.0 (3.2-5.4) |
| Podocyte number per glomerulus | 615 (474-752) |
| Foot Process Width (nm) | 453 (402-520) |
| Podocyte detachment (%) | 0.4 (0.0-1.4) |
| Fenestrated endothelium (%) | 26.2 (21.8-31.7) |
| Globally sclerotic glomeruli (%) density (p2 | 5.4 (0.0-17.7) |
| Glomerular filtration surface ($\mu^2$ $\mu^3$) | |
| Cortical interstitial fractional volume (%) | 29.5 (24.6-33.0) |

The association between AGEs and structure for each AGE were tested against each renal structural variable by linear regression with and without adjustment for covariates.

The following covariates were taken as the mean value of the baseline and biopsy examinations age, sex, treatment assignment, diabetes duration, HbA1c, and mean arterial pressure, GFR by iothalamate clearance, and albumin/creatinine ratio (ACR).

As seen in the Figures, MG-H1, CEL and GHI showed significant adjusted relationships with the main structural parameters of diabetic nephropathy.

AGEs and Renal Structural change: Characteristics of the 95 participants who underwent a kidney biopsy and for whom AGE/OP concentrations were available near the time of biopsy are presented in Table 17. Forty-nine (52%) of those who underwent kidney biopsy had ACR<30 mg/g and 46 (48%) had ACR=30-299 mg/g at enrollment into the clinical trial. AGE/OP concentrations were measured in serum samples obtained a median of 85 (IQR=43 to 87) days from the kidney biopsy. In univariate models (Table 20) all dicarbonyl-derived compounds were significantly and positively correlated with the proportion of globally sclerotic glomeruli (r=0.25 to 0.33, P<0.001 to 0.02), mesangial fractional volume per glomerulus (r=0.25 to 0.30, P<0.001 to 0.01), and cortical interstitial fractional volume (r=0.25 to 0.38, P=0.003 to 0.02). All AGEs, with the exception of 3-deoxyglucosone hydroimidazolone, were negatively associated with total filtration surface per glomerulus (r=−0.34 to −0.26; P<0.001 to 0.01). Glomerular volume was negatively associated with carboxyethyl lysine and methylglyoxal hydroimidazolone (r=−0.22, P=0.03 and r=−0.21, P=0.04, respectively). Filtration surface density was negatively associated with glyoxal hydroimidazolone (r=−0.24, P=0.02). Fenestrated endothelium was negatively associated with carboxymethyl lysine (r=−0.25, P=0.02). Podocyte foot process width was positively associated with glyoxal hydroimidazolone (r=0.21, P=0.04). One participant had a foot process width 6.5 standard deviations above the mean; removal of this outlier strengthened the relationship with glyoxal hydroimidazolone (r=0.29, P=0.004). Neither of the OPs was associated with any structural measures.

Although multivariate adjustment (Models A and B) attenuated many of the observed relationships (Table 20), all dicarbonyl-derived AGEs remained associated with at least one morphometric parameter after full adjustment. In model B, carboxyethyl lysine and methylglyoxal hydroimidazolone were positively correlated with cortical interstitial fractional volume (partial r=0.27, P=0.01, and partial r=0.28, P=0.008, respectively) and carboxymethyl lysine, carboxyethyl lysine and methylglyoxal hydroimidazolone with mesangial fractional volume (partial r=0.25, P=0.02, partial r=0.23, P=0.03 and partial r=0.31, P=0.003, respectively). Glyoxyl hydroimidazolone and methylglyoxal hydroimidazolone were negatively correlated with total filtration surface per glomerulus (partial r=−0.26, P=0.01 and partial r=−0.21, P=0.05, respectively). 3-deoxyglucosone hydroimidazolone was positively correlated with percentage of globally sclerotic glomeruli (partial r=0.30, P=0.005). Finally, carboxymethyl lysine was negatively associated with the percentage of fenestrated endothelium.

In Table 20, P values are shown in brackets after Pearson's correlation coefficient. P values<0.05 are shown in bold. Model A was adjusted for age, sex, treatment assignment, diabetes duration, HbA1c and mean arterial pressure. Model B was adjusted for Model A covariates+glomerular filtration rate.

TABLE 20

Pearson's Correlations for the Associations Between Advanced Glycation
End-Products, Oxidative End-Products and Renal Morphometric Variables

| | % GS | $V_G$ | VvInt | VvMes | $S_v$ | TFS | GBM |
|---|---|---|---|---|---|---|---|
| | | | | Univariate Model | | | |
| MetSO | 0.10(0.34) | −0.03(0.78) | 0.06(0.58) | 0.08(0.47) | −0.04(0.70) | −0.08(0.44) | 0.01(0.90) |
| 2-AAA | 0.01(0.89) | −0.05(0.63) | −0.06(0.58) | 0.01(0.96) | 0.18(0.08) | 0.09(0.38) | −0.20(0.05) |
| CML | 0.25(0.02) | −0.07(0.51) | 0.30(0.003) | 0.28(0.006) | −0.18(0.08) | −0.26(0.02) | 0.15(0.15) |
| GH1 | 0.28(0.007) | −0.11(0.31) | 0.29(0.004) | 0.25(0.01) | −0.24(0.02) | −0.34(<0.001) | 0.12(0.24) |
| CEL | 0.32(0.002) | −0.22(0.03) | 0.30(0.003) | 0.32(0.002) | −0.13(0.20) | −0.32(0.001) | −0.02(0.82) |
| MGH1 | 0.25(0.01) | −0.21(0.04) | 0.25(0.02) | 0.38(<0.001) | −0.17(0.10) | −0.34(<0.001) | 0.03(0.74) |
| 3DGHI | 0.33(<0.001) | −0.05(0.62) | 0.26(0.01) | 0.30(0.004) | −0.12(0.25) | −0.19(0.07) | 0.17(0.09) |
| | | | | Model A | | | |
| MetSO | 0.06(0.59) | −0.07(0.52) | 0.08(0.48) | 0.08(0.43) | −0.04(0.74) | −0.11(0.33) | 0.04(0.71) |
| 2-AAA | −0.02(0.86) | −0.06(0.60) | −0.09(0.41) | −0.03(0.79) | 0.18(0.09) | 0.09(0.41) | −0.22(0.04) |
| CML | 0.18(0.08) | −0.01(0.93) | 0.27(0.01) | 0.25(0.02) | −0.15(0.16) | −0.21(0.05) | 0.19(0.08) |
| GH1 | 0.20(0.05) | −0.07(0.51) | 0.35(<0.001) | 0.23(0.03) | −0.28(0.009) | −0.36(<0.001) | 0.22(0.04) |
| CEL | 0.20(0.07) | −0.10(0.36) | 0.23(0.03) | 0.26(0.01) | −0.07(0.49) | −0.20(0.06) | 0.01(0.91) |
| MGH1 | 0.18(0.10) | −0.17(0.10) | 0.24(0.02) | 0.34(0.001) | −0.15(0.15) | −0.31(0.004) | 0.05(0.63) |
| 3DGHI | 0.28(0.008) | −0.04(0.72) | 0.15(0.15) | 0.20(0.07) | −0.07(0.54) | −0.13(0.21) | 0.12(0.26) |
| | | | | Model B | | | |
| MetSO | 0.04(0.69) | −0.07(0.50) | 0.11(0.29) | 0.11(0.32) | −0.07(0.54) | −0.16(0.13) | 0.03(0.75) |
| 2-AAA | −0.004(0.97) | −0.08(0.45) | −0.004(0.97) | −0.003(0.98) | 0.11(0.31) | −0.01(0.95) | −0.20(0.06) |
| CML | 0.16(0.13) | 0.06(0.59) | 0.27(0.001) | 0.25(0.02) | −0.13(0.22) | −0.12(0.27) | 0.17(0.12) |
| GH1 | 0.19(0.08) | 0.003(0.98) | 0.28(0.008) | 0.19(0.08) | −0.18(0.09) | −0.26(0.01) | 0.16(0.13) |
| CEL | 0.17(0.12) | −0.02(0.89) | 0.02(0.07) | 0.23(0.03) | −0.03(0.81) | −0.11(0.32) | −0.02(0.85) |
| MGH1 | 0.16(0.15) | −0.08(0.48) | 0.20(0.06) | 0.31(0.003) | −0.10(0.37) | −0.21(0.047) | −0.01(0.95) |
| 3DGHI | 0.30(0.005) | 0.06(0.60) | 0.13(0.22) | 0.19(0.08) | −0.05(0.67) | −0.03(0.76) | 0.11(0.30) |

| | # E + M | # Podo | FPW* | % PD | % Fen |
|---|---|---|---|---|---|
| | | | Univariate Model | | |
| MetSO | 0.08(0.45) | 0.11(0.27) | 0.11(0.29) | 0.13(0.20) | −0.14(0.17) |
| 2-AAA | −0.05(0.60) | −0.001(0.99) | 0.03(0.81) | −0.01(0.91) | 0.04(0.72) |
| CML | 0.15(0.16) | −0.01(0.93) | 0.03(0.76) | 0.03(0.74) | −0.25(0.02) |
| GH1 | 0.02(0.83) | −0.01(0.92) | 0.29(0.004) | 0.04(0.67) | −0.14(0.19) |
| CEL | 0.07(0.47) | −0.13(0.21) | 0.09(0.39) | 0.03(0.79) | −0.20(0.05) |
| MGH1 | −0.01(0.93) | −0.03(0.74) | 0.17(0.09) | −0.04(0.72) | −0.06(0.57) |
| 3DGHI | 0.19(0.06) | 0.03(0.77) | 0.11(0.27) | 0.06(0.58) | −0.08(0.45) |
| | | | Model A | | |
| MetSO | 0.05(0.64) | 0.14(0.20) | 0.14(0.20) | 0.14(0.18) | −0.13(0.24) |
| 2-AAA | −0.06(0.55) | 0.05(0.66) | 0.02(0.83) | −0.03(0.77) | 0.01(0.94) |
| CML | 0.15(0.16) | 0.05(0.63) | 0.06(0.59) | 0.01(0.95) | −0.24(0.02) |
| GH1 | 0.05(0.63) | 0.01(0.90) | 0.33(0.002) | 0.05(0.63) | −0.20(0.06) |
| CEL | 0.10(0.35) | −0.02(0.87) | 0.13(0.24) | −0.04(0.73) | −0.19(0.07) |
| MGH1 | −0.01(0.95) | 0.002(0.99) | 0.16(0.14) | −0.08(0.46) | −0.06(0.55) |
| 3DGHI | 0.11(0.28) | 0.08(0.48) | 0.05(0.63) | −0.001(0.99) | −0.06(0.61) |
| | | | Model B | | |
| MetSO | 0.03(0.76) | 0.13(0.23) | 0.15(0.17) | 0.15(0.17) | −0.15(0.15) |
| 2-AAA | −0.05(0.62) | 0.01(0.91) | 0.05(0.65) | −0.02(0.86) | −0.07(0.54) |
| CML | 0.19(0.08) | 0.06(0.55) | 0.05(0.66) | 0.003(0.98) | −0.23(0.03) |
| GH1 | 0.10(0.35) | 0.07(0.53) | 0.32(0.003) | 0.04(0.73) | −0.11(0.29) |
| CEL | 0.14(0.19) | 0.004(0.97) | 0.11(0.30) | −0.05(0.68) | −0.16(0.14) |

TABLE 20-continued

Pearson's Correlations for the Associations Between Advanced Glycation
End-Products, Oxidative End-Products and Renal Morphometric Variables

| | | | | | | |
|---|---|---|---|---|---|---|
| | MGH1 | 0.05(0.67) | 0.03(0.78) | 0.14(0.19) | −0.09(0.40) | −0.01(0.93) |
| | 3DGHI | 0.16(0.14) | 0.09(0.43) | 0.05(0.67) | −0.005(0.96) | −0.04(0.73) |

Abbreviations for Analytes follows:
MetSO = methionine sulfoxide;
2-AAA = 2-aminoadipic acid;
CML = carboxymethyl lysine;
GH1 = glyoxal hydroimidazolone;
CEL = carboxyethyl lysine;
MGH1 = methylglyoxal hydroimidazolone;
3DGHI = 3 deoxyglucosone hydroimidazolone, and for renal structural parameters:
% GS = % global glomerular sclerosis;
VG = mean glomerular volume (×10⁶/μm3);
VvInt = cortical interstitial fractional volume (%);
VvMes = mesangial fractional volume (%);
SV = glomerular filtration surface density (μm2/μm3);
TFS = total filtration surface per glomerulus (×105/μm3);
GBM = glomerular basement membrane width (nm);
E + M = number of endothelial + mesangial cells per glomerulus;
Podo = podocyte number per glomerulus;
FPW = foot process width (nm);
% PD = % podocyte detachment;
% Fen = % fenestrated endothelium.
*Correlation was analyzed with the exclusion of one outlier.

The partial correlations of each AGE/OP with relevant structural variables are shown in the Figures. For illustration, partial residual regression plots of methylglyoxal hydroimidazolone with cortical interstitial fractional volume and total filtration surface per glomerulus (FIG. 6) and fractional mesangial volume and total filtration surface are shown in FIG. 7. We found no interactions between losartan treatment assignment and any of the AGEs/OPs, indicating that the relationship between these biomarkers and the morphometric variables was not modified by treatment.

AGEs and Renal Function Loss: During a median follow-up of 8.0 (4.9 to 13.1) years, the primary endpoint of RFL (≥40% decline in GFR) occurred in 104 (62%) of the participants. In univariate Cox models, a higher concentration of methylglyoxal hydroimidazolone at baseline was associated with a higher risk of RFL (Table 21). After multivariable adjustment (Model C), carboxyethyl lysine (HR per doubling=1.60, 95% CI 1.08 to 2.37) and methylglyoxal hydroimidazolone (HR=1.30, 95% CI 1.02 to 1.65) each predicted RFL. Adjustment for both GFR and ACR strengthened the association between these compounds and RFL, in comparison with models A and B (Table 21). Table 21 provides data concerning the loss of renal function presented as hazard ratio (95% confidence interval) from study participants. Data are presented as hazard ratio (95% confidence interval). The data in Table 21 are presented as hazard ratio (95% confidence interval). Hazard ratios are given per doubling of the AGE variable. P values<0.05 are shown in bold. Model A was adjusted for age, sex, treatment assignment, diabetes duration, HbA1c and mean arterial pressure. Model B was adjusted for Model A covariates+ glomerular filtration rate.

TABLE 21

Cox Proportional Hazards Model for the Risk of >40% Decline In GFR from Baseline
Associated with a Doubling of the Serum Concentration of
Advanced Glycation End-Products and Oxidative End-Products

| Variable | Univariate | Model A | Model B | Model C |
|---|---|---|---|---|
| Cox models | | | | |
| MetSO | 0.77 (0.46-1.31) P = 0.34 | 0.98 (0.57-1.70) P = 0.94 | 0.93 (0.54-1.62) P = 0.80 | 0.97 (0.56-1.69) P = 0.88 |
| 2-AAA | 0.95 (0.66-1.39) P = 0.80 | 0.96 (0.63-1.46) P = 0.83 | 0.82 (0.55-1.24) P = 0.35 | 0.82 (0.55-1.22) P = 0.38 |
| CML | 1.35 (0.99-1.85) P = 0.06 | 1.30 (0.91-1.85) P = 0.15 | 1.38 (0.97-1.96) P = 0.07 | 1.39 (0.97-1.98) P = 0.06 |
| GH1 | 0.96 (0.59-1.58) P = 0.88 | 1.00 (0.54-1.85) P = 0.998 | 1.27 (0.69-2.32) P = 0.45 | 1.29 (0.70-2.38) P = 0.40 |
| CEL | 1.29 (0.93-1.80) P = 0.12 | 1.35 (0.92-1.97) P = 0.13 | 1.59 (1.07-2.35) P = 0.02 | 1.60 (1.08-2.37) P = 0.01 |
| MGH1 | 1.26 (1.03-1.56) P = 0.03 | 1.27 (1.00-1.61) P = 0.046 | 1.28 (1.01-1.63) P = 0.04 | 1.30 (1.02-1.65) P = 0.03 |

TABLE 21-continued

Cox Proportional Hazards Model for the Risk of >40% Decline In GFR from Baseline
Associated with a Doubling of the Serum Concentration of
Advanced Glycation End-Products and Oxidative End-Products

| Variable | Univariate | Model A | Model B | Model C |
|---|---|---|---|---|
| 3DGHI | 1.21 (0.93-1.58) P = 0.15 | 1.16 (0.86-1.57) P = 0.32 | 1.20 (0.88-1.64) P = 0.25 | 1.21 (0.88-1.64) P = 0.21 |

*competing risk = all-cause death

Sensitivity Analyses for AGEs and Renal Function Loss: Table 22 shows the results of the remaining sensitivity analyses. When the five participants who developed ESRD but did not meet the GFR criteria for RFL were included as cases of RFL, carboxymethyl lysine, in addition to carboxyethyl lysine and methylglyoxal hydroimidazolone, each predicted RFL in model C (HR=1.44, 95% CI=1.02 to 2.04; HR=1.68, 95% CI=1.14 to 2.46; and HR=1.32, 95% CI=1.05 to 1.67, respectively). When RFL was ascertained by linear imputation, the same 109 participants reached the RFL endpoint, and the findings were equivalent to the primary analyses. Data in Table 22 are presented as hazard ratio (95% confidence interval). Hazard ratios are given per 1SD increase of the AGE variable. P values<0.05 are shown in bold. Sections 4, 5, and 6 of Table 22 encompass: (4) Prespecified outcome: the prespecified outcome from the clinical trial was a decline in GFR to ≤60 ml/min or to half the baseline value in subjects who entered the study with a GFR<120 ml/min; (5) ESRD without RFL considered as cases: the five individuals who developed ESRD without reaching the RFL endpoint at a research examination were included as cases of RFL, with the last known research examination considered as the onset of RFL; and (6) Imputation method: linear GFR slope was computed from the last two GFR measurements in each participant in order to identify the most accurate date for the event. Further in Table 22, the statistical models are designed as follows: (1) Model A was adjusted for age, sex, treatment assignment, diabetes duration, HbA1c and mean arterial pressure; (2) Model B was adjusted for Model A covariates+glomerular filtration rate; and (3) Model C was adjusted for Model B covariates+albumin/creatinine ratio.

TABLE 22

Cox Proportional Hazards Models for the Risk of Renal Outcomes
According to Various Sensitivity Analyses

| Variable | Univariate | Model A | Model B | Model C |
|---|---|---|---|---|
| #4 Prespecified outcome | | | | |
| MetSO | 1.28 (0.53-3.10) P = 0.58 | 1.4 8(0.61-3.6) P = 0.39 | 1.48 (0.61-3.62) P = 0.39 | 1.61 (0.65-3.98) P = 0.30 |
| 2-AAA | 0.73 (0.38-1.38) P = 0.33 | 0.63 (0.31-1.31) P = 0.22 | 0.60 (0.28-1.30) P = 0.19 | 0.61 (0.29-1.28) P = 0.19 |
| CML | 2.13 (1.22-3.72) P = 0.01 | 1.62 (0.87-3.00) P = 0.13 | 1.62 (0.87-3.01) P = 0.13 | 1.62 (0.87-3.01) P = 0.13 |
| GH1 | 2.32 (1.10-4.88) P = 0.03 | 2.36 (0.97-5.75) P = 0.06 | 2.37 (0.97-5.79) P = 0.06 | 2.41 (0.97-5.97) P = 0.06 |
| CEL | 2.34 (1.34-4.09) P = 0.003 | 2.00 (1.02-3.92) P = 0.04 | 2.07 (1.03-4.16) P = 0.04 | 2.14(1.06-4.34) P = 0.03 |
| MGH1 | 1.94 (1.36-2.77) P = 0.0002 | 1.75 (1.14-2.68) P = 0.01 | 1.75 (1.14-2.68) P = 0.01 | 1.80(1.17-2.77) P = 0.01 |
| 3DGHI | 1.86 (1.30-2.67) P = 0.001 | 1.57 (0.99-2.46) P = 0.05 | 1.57 (0.99-2.49) P = 0.05 | 1.62 (1.03-2.55) P = 0.04 |
| #5 Patients reaching ESRD without RFL were considered as cases at time of last exam | | | | |
| MetSO | 0.79 (0.47-1.32) P = 0.37 | 0.99 (0.58-1.7) P = 0.98 | 0.96 (0.56-1.65) P = 0.89 | 1.00 (0.58-1.71) P = 0.99 |
| 2-AAA | 1.02 (0.71-1.47) P = 0.92 | 1.01 (0.67-1.52) P = 0.98 | 0.88 (0.59-1.32) P = 0.55 | 0.90 (0.61-1.33) P = 0.6 |
| CML | 1.38 (1.02-1.88) P = 0.04 | 1.31 (0.93-1.85) P = 0.13 | 1.40 (0.99-1.97) P = 0.06 | 1.44 (1.02-2.04) P = 0.04 |
| GH1 | 1.04 (0.64-1.68) P = 0.88 | 1.07 (0.59-1.94) P = 0.83 | 1.36 (0.75-2.44) P = 0.31 | 1.41 (0.78-2.56) P = 0.26 |
| CEL | 1.34 (0.97-1.85) P = 0.07 | 1.37 (0.95-1.99) P = 0.09 | 1.61 (1.10-2.36) P = 0.01 | 1.68 (1.14-2.46) P = 0.01 |
| MGH1 | 1.28 (1.04-1.57) P = 0.02 | 1.27 (1.01-1.59) P = 0.04 | 1.29 (1.02-1.62) P = 0.03 | 1.32 (1.05-1.67) P = 0.02 |
| 3DGHI | 1.26 (0.98-1.63) P = 0.07 | 1.22 (0.91-1.63) P = 0.18 | 1.27 (0.94-1.71) P = 0.13 | 1.29 (0.95-1.73) P = 0.10 |
| #6 Imputation method | | | | |
| MetSO | 0.74 (0.44-1.23) P = 0.24 | 0.94 (0.55-1.61) P = 0.83 | 0.91 (0.53-1.55) P = 0.72 | 0.93 (0.54-1.59) P = 0.79 |
| 2-AAA | 1.00 (0.69-1.46) P = 0.99 | 1.00 (0.66-1.51) P = 0.99 | 0.86 (0.57-1.29) P = 0.46 | 0.86 (0.58-1.27) P = 0.44 |

TABLE 22-continued

Cox Proportional Hazards Models for the Risk of Renal Outcomes
According to Various Sensitivity Analyses

| Variable | Univariate | Model A | Model B | Model C |
|---|---|---|---|---|
| CML | 1.41 (1.03-1.92) | 1.30 (0.92-1.84) | 1.38 (0.97-1.94) | 1.41 (0.99-2.00) |
|  | P = 0.03 | P = 0.14 | P = 0.07 | P = 0.05 |
| GH1 | 1.06 (0.65-1.70) | 1.08 (0.6-1.95) | 1.32 (0.74-2.37) | 1.36 (0.75-2.46) |
|  | P = 0.83 | P = 0.79 | P = 0.35 | P = 0.31 |
| CEL | 1.35 (0.98-1.87) | 1.38 (0.95-1.99) | 1.58 (1.08-2.31) | 1.63 (1.11-2.39) |
|  | P = 0.07 | P = 0.09 | P = 0.02 | P = 0.01 |
| MGH1 | 1.31 (1.06-1.61) | 1.29 (1.03-1.62) | 1.30 (1.03-1.63) | 1.32 (1.05-1.67) |
|  | P = 0.01 | P = 0.03 | P = 0.03 | P = 0.02 |
| 3DGHI | 1.31 (1.01-1.70) | 1.25 (0.93-1.68) | 1.30 (0.95-1.76) | 1.33 (0.98-1.80) |
|  | P = 0.04 | P = 0.14 | P = 0.10 | P = 0.07 |

MetSO = methionine sulfoxide;
2-AAA = 2-aminoadipic acid;
CML = carboxymethyl lysine;
GH1 = glyoxal hydroimidazolone;
CEL = carboxyethyl lysine;
MGHI = methylglyoxal hydroimidazolone;
3DGHI = 3 deoxyglucosone hydroimidazolone.

In preferred embodiments se studies of specific glycation end-products (MG-H1, CEL, and GHI) support a role for elevated dicarbonyl levels in the development of diabetic nephropathy in type 2 diabetes; the role of these specific AGE biomarkers in progression of diabetic nephropathy is confirmed by documenting correlations with clinical progression of diabetic nephropathy, and specific related morphological renal changes. Clinical use of new biomarkers such as these will allow early individualized treatments to prevent complications.

Example 3

Methionine Sulfoxide (METSO) Levels in Plasma and Prediction of Cardiovascular Disease (CVD) Outcomes in Type 1 Diabetes The association and predictive value of oxidation products (OPs) and advanced glycation end products (AGEs) as they relate to cardiovascular related disease events CVD events in 30 years of DCCT/EDIC trial data was analyzed. In particular, the levels of methionine sulfoxide (MetSO), carboxyethyllysine (CEL), and 3 deoxyglucosone hydroimidazolone (3DGH) were obtained, stored, processed, and analyzed according to the methods described above using a case-control design as follows.

Methods of Liquid Chromatography/Triple Quadrupole Mass Spectroscopy (LC-MS/MS) described above were used to analyze plasma samples from 459 participants in DCCT and EDIC studies. Ninety-three participants had symptoms of cardiovascular disease (CVD), while the remaining 366 participants were non-CVD controls, CVD was indicated by nonfatal myocardial infract (MI) and strokes (ischemic, hemorrhagic, and/or transient ischemic attack), CVD related mortality, confirmed angina, congestive heart failure, and coronary revascularization. The plasma samples were taken at baseline, year 1, DCCT closeout, and year 1-2 of studies.

Cox models were employed to look at association between biomarkers as fixed (baseline and early EDIC) or time-dependent (all 4 time points) covariates and CVD outcome.

To assess prediction improvement, C-statistic was computed for biomarkers which were significantly associated with the outcomes in fully adjusted models.

Baseline CEL was associated with CVD (p=0.03, HR 1.15) when fully adjusted for all covariates (i.e., Age, HbA1c, body mass index [BMI], high density lipoprotein [HDL], low density lipoprotein [LDL], sex, systolic blood pressure [SBP], and diastolic blood pressure [DBP]), while MetSO at beginning of EDIC and in the time dependent analysis, was strongly inversely associated with cardiovascular outcomes (p<0.001 and HR 0.58 and 0.61 respectively). Adding MetSO to the model significantly increased the predictive c-statistic from 0.711 to 0.783 (p<0.001) when added to the other covariates (mentioned above).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:
1. A method for determining a risk or rate of an individual of developing cardiovascular disease, wherein the individual suffers from diabetes, said method comprising:
   determining a level of one or more biomarkers purified from a biological sample obtained from the individual;
   wherein said one or more biomarkers are selected from the group comprising lysine advanced glycation end products, arginine advanced glycation end products and oxidation products;
   comparing the determined biomarker levels to standard values, wherein the level of said biomarkers indicate the risk or rate of developing cardiovascular disease;
   wherein said one or more biomarkers further comprises methionine sulfoxide (MetSO), and wherein elevated levels of MetSO in the individual as compared to a standard value of MetSO indicates a decrease in the risk or rate of developing cardiovascular disease, and depressed levels of MetSO in the individual as compared to the standard value of MetSO indicates an increase in the risk or rate of developing cardiovascular disease.

2. The method of claim 1, wherein the one or more biomarkers further comprise $N_\varepsilon$-carboxy methyl-lysine (CML), $N_\varepsilon$-carboxy ethyl-lysine (CEL), glyoxal hydroimidazolone (GH1), methylglyoxal hydroimidazolone (MG-H1), 3-deoxyglucosone hydroimidazolone (3DGH), 2-aminoadipic acid (2-AAA) or 3-nitrotyrosine (3-NT).

3. The method of claim 1, wherein the advanced glycation end products are selected from the group comprising $N_\varepsilon$-carboxy ethyl-lysine (CEL), $N_\varepsilon$-carboxy methyl-lysine (CML), and methylglyoxal hydroimidazolone (MG-H1).

4. The method of claim 1 comprising determining the level of said one or more biomarkers using Liquid Chromatography/Triple Quadrupole Mass Spectrometry (LC-MS/MS) to quantify said biomarkers.

5. The method of claim 4, wherein the LC-MS/MS further comprises a stationary phase comprising C18 with an ion pairing agent.

6. The method of claim 1, wherein said sample is a blood, urine, or plasma sample.

7. The method of claim 6, wherein said plasma sample is an ultrafiltrate.

8. The method of claim 7, wherein said ion paring agent is heptafluorobutyric acid.

9. The method of claim 1, wherein the individual is determined to be at risk of developing cardiovascular disease.

10. The method of claim 1, further comprising providing a report describing said risk or rate of developing cardiovascular disease.

11. The method of claim 1, further comprising providing recommending cardiovascular disease treatments for said individual.

* * * * *